(12) United States Patent
Ehteshami et al.

(10) Patent No.: US 12,383,410 B2
(45) Date of Patent: Aug. 12, 2025

(54) DYNAMIC INTER VERTEBRAL SPACER IMPLANT

(71) Applicant: Additive Implants, Inc., Phoenix, AZ (US)

(72) Inventors: John R. Ehteshami, Paradise Valley, AZ (US); Mahyar Zoghi, Phoenix, AZ (US)

(73) Assignee: Additive Implants, Inc., Phoenix, AZ (US)

( * ) Notice: Subject to any disclaimer, the term of this patent is extended or adjusted under 35 U.S.C. 154(b) by 115 days.

(21) Appl. No.: 17/589,264

(22) Filed: Jan. 31, 2022

(65) Prior Publication Data

US 2022/0151798 A1 May 19, 2022

Related U.S. Application Data

(63) Continuation of application No. 16/580,865, filed on Sep. 24, 2019, now Pat. No. 11,234,838, which is a continuation-in-part of application No. 16/383,142, filed on Apr. 12, 2019, now Pat. No. 11,045,328, which is a continuation of application No. 16/125,640, filed on Sep. 7, 2018, now Pat. No. 10,299,938.

(51) Int. Cl.
*A61F 2/44* (2006.01)
*A61F 2/30* (2006.01)
*A61F 2/46* (2006.01)

(52) U.S. Cl.
CPC .............. *A61F 2/447* (2013.01); *A61F 2/442* (2013.01); *A61F 2002/30069* (2013.01); *A61F 2002/30112* (2013.01); *A61F 2002/30179* (2013.01); *A61F 2002/30265* (2013.01); *A61F 2002/30324* (2013.01); *A61F 2002/30593* (2013.01); *A61F 2002/30622* (2013.01); *A61F 2002/30772* (2013.01); *A61F 2002/4629* (2013.01)

(58) Field of Classification Search
CPC .................................. A61F 2/447; A61F 2/442
See application file for complete search history.

(56) References Cited

U.S. PATENT DOCUMENTS

| | | | |
|---|---|---|---|
| 11,432,941 B2 * | 9/2022 | Biedermann | ........... A61F 2/446 |
| 2020/0093612 A1 * | 3/2020 | Blain | ................... A61F 2/4611 |

\* cited by examiner

*Primary Examiner* — Sameh R Boles
(74) *Attorney, Agent, or Firm* — David Meibos; Maywood IP Law

(57) ABSTRACT

Intervertebral spacer implants with dynamic load spreading features responsive to external loads and having attachment mechanisms. The dynamic load spreading features having a native state and a loaded state, which complements vertebral end plate geometry and disperses load to the epiphyseal rim.

13 Claims, 13 Drawing Sheets

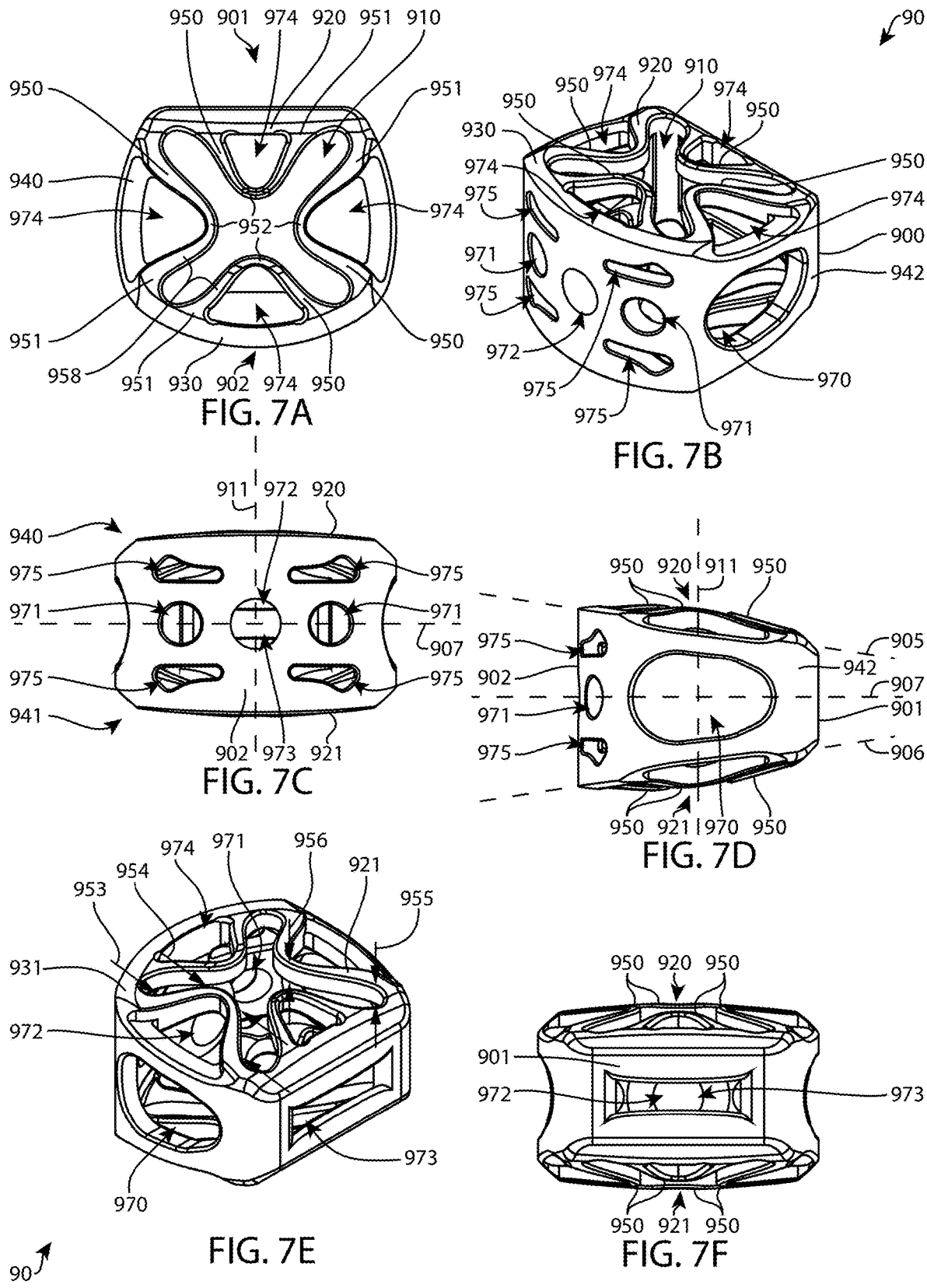

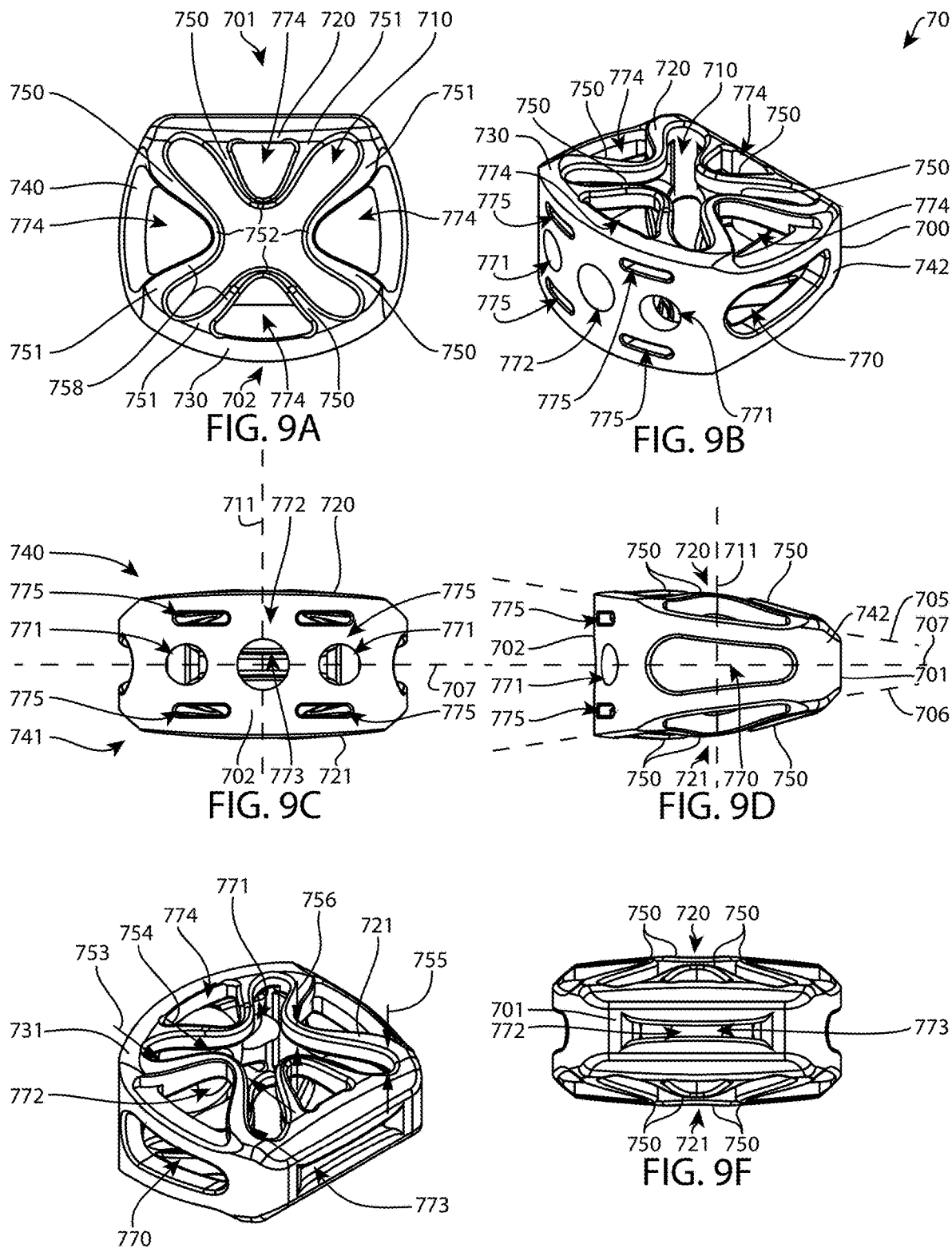

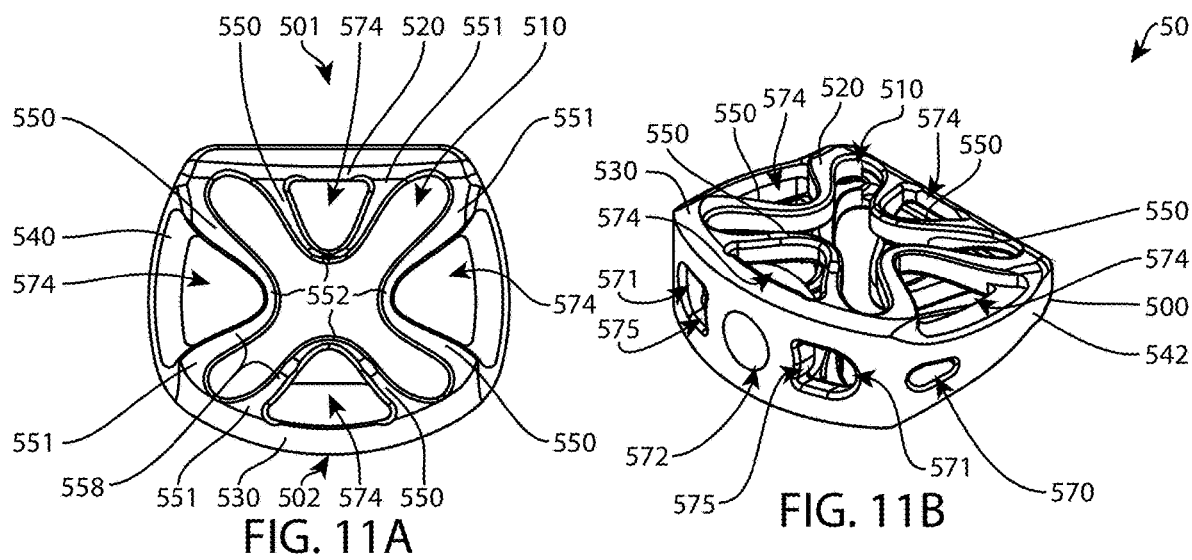
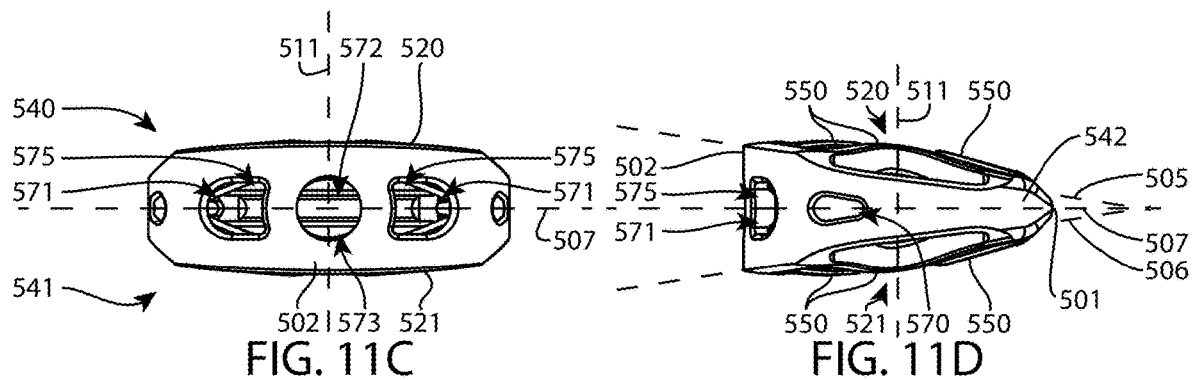
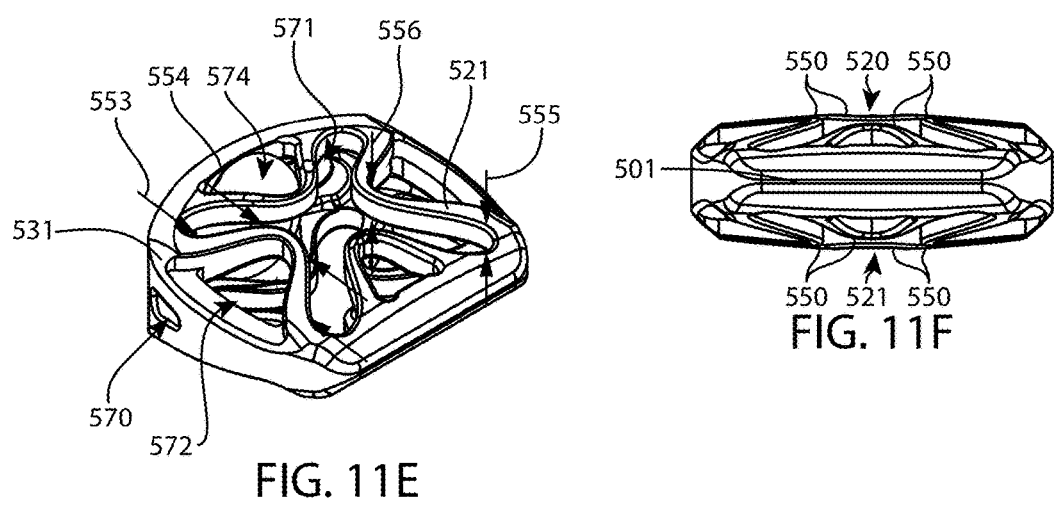

DYNAMIC INTER VERTEBRAL SPACER IMPLANT

CROSS-REFERENCE TO RELATED APPLICATIONS

This application is a continuation of U.S. patent application Ser. No. 16/580,865 filed on Sep. 24, 2019, entitled DYNAMIC INTERVERTEBRAL SPACER IMPLANT, which is a continuation-in-part of U.S. patent application Ser. No. 16/383,142 filed on Apr. 12, 2019, entitled DYNAMIC INTERVERTEBRAL SPACER IMPLANT, which issued on Jun. 29, 2021 as U.S. Pat. No. 11,045,328. U.S. patent application Ser. No. 16/383,142 is a continuation of U.S. patent application Ser. No. 16/125,640 filed on Sep. 7, 2018, entitled DYNAMIC INTERVERTEBRAL SPACER IMPLANT, which issued on May 28, 2019 as U.S. Pat. No. 10,299,938.

The foregoing are incorporated herein by reference as though set forth in their entirety.

TECHNICAL FIELD

The present technology relates to intervertebral spacer implants. More specifically, the present technology relates to spinal interbody fusion implants (spacers) having dynamic elements on at least one side of the implant body. Implants with dynamic or flexible elements allow the spreading of intervertebral load across the end plate of the vertebral body. Increasing the contact area from a point to a large surface and particularly loading the vertebral body toward the outer rim, where the bone density is generally higher, reduces implant subsidence. Additionally, maintaining several points of contact across the end plate reduces implant movement. Lastly, having dynamic elements reduces the overall stiffness of the spacer and allows the bone graft material packed within it to carry part of the load that is being transferred from one adjacent vertebral body to the vertebral body on the opposite side of the spacer. This disclosure is made in the context of intervertebral implants, but the principles disclosed herein are applicable in locations throughout the body.

BACKGROUND

Intervertebral disc pathology can be the result of many factors including injury, aging, environmental factors, tumors, infection, and genetics. Intervertebral disc pathology can result in the absence of physiological loading of vertebral end plates resulting in instability or degenerative changes over time, which may lead to spinal stenosis and neurological complications.

Several surgical techniques have been developed to address intervertebral disc pathology and associated diseases that affect the verbal endplates, to which the discs transmit their load. Spinal decompression with or without disc removal and fusion has become a recognized surgical procedure for mitigating spinal column pain by restoring biomechanical and anatomical integrity to the spine. Spinal fusion is recommended based on a variety of clinical indications. Fusion techniques may involve the excision of intervertebral disc material and the preparation of the disc space for receiving an implant to aid in fusion and transmission of the load from vertebrae and maintain vertebral column shape after the fusion process. The surgically-placed implants (spacers) can rest on the exposed vertebral endplates.

Spinal fusion procedures are generally conducted using a posterior or an anterior approach. Anterior cervical interbody fusion (ACDF) procedures generally have the advantages of reduced operative times, lower infection rate, and reduced blood loss. Further, anterior procedures do not interfere with the posterior anatomic structure of the spine. Anterior procedures also minimize scarring within the spinal canal and are advantageous from a structural and biomechanical perspective. The generally preferred anterior procedures are particularly advantageous in providing improved access to the disc space, and correspondingly better endplate preparation.

Several inter-body implant systems have been introduced to facilitate inter-body fusion. Traditional threaded implants or cages, of varying shapes and material, are typically packed with bone graft material and surgically placed in the intervertebral disc space. However, a relatively small portion of the vertebral endplate is in contacted with these implants. These implant bodies often engage the softer cancellous bone in the center of the vertebra, rather than the stronger cortical bone, the uncinate process, or the apophyseal rim of the vertebral endplate. The seating of threaded cylindrical implants may also compromise biomechanical integrity by reducing the area in which to distribute mechanical forces, thus increasing the apparent stress experienced by both the implant and vertebrae. Further, a substantial uncontrolled risk of implant subsidence (defined as sinking or settling) into the softer cancellous bone of the vertebral body may arise from such improper seating.

Even open ring-shaped cage or spacer implant systems, generally shaped to mimic the anatomical contour of the vertebral body, lack the ability to complement specific stiffness of the patient's bone. Traditional ring-shaped cages are generally comprised of allograft bone material, harvested from the human donors. Such allograft bone material restricts the usable size and shape of the resultant implant. For example, many of these ring-shaped bones generally have a medial-lateral width of less than 25 mm for the lumbar spine and 14 mm for cervical spine. Therefore, these allograft cages may not be of a sufficient size to contact the strong cortical bone, the uncinate process, or apophyseal rim of the vertebral endplate. These size-limited implant systems may also poorly accommodate related instrumentation such as drivers, reamers, distractors, and the like. For example, these implant systems may lack sufficient structural integrity to withstand repeated impact and may fracture during implantation. Further, other traditional non-allograft ring-shaped cage systems may be size-limited due to various and complex supplemental implant instrumentation, which may obstruct the disc space while requiring greater exposure of the operative field. These supplemental implant instrumentation systems also generally increase the instrument load on the surgeon.

The surgical procedure corresponding to an implant system should preserve as much vertebral endplate bone surface as possible by minimizing the amount of bone removed. This vertebral endplate bone surface, or subchondral bone, is generally much stronger than the underlying cancellous bone. Preservation of the endplate bone stock ensures biomechanical integrity of the endplates and minimizes the risk of implant subsidence. Thus, proper interbody implant design should provide for optimal seating of the implant while utilizing the maximum amount of available supporting vertebral bone stock.

Traditional interbody spinal implants generally do not seat properly on the preferred structural bone located near the apophyseal rim of the vertebral body, which is primarily composed of preferred dense subchondral bone. Accordingly, there is a need in the art for interbody spinal implants which better utilize the structurally supportive bone of the apophyseal rim.

In summary, separate challenges can be identified as inherent in traditional anterior spinal fusion devices: 1) end-plate preparation; 2) implant retention; 3) implant subsidence; 4) bone graft volume; 5) implant incorporation with vertebral bone; and 6) radiographic visualization.

1. End-Plate Preparation

There are three traditional end-plate preparation methods. The first is aggressive end-plate removal with box chisel-types of tools to create a match between end-plate geometry and implant geometry. In the process of aggressive end-plate removal, however, the end-plates are typically destroyed. Such destruction means that the load-bearing implant is pressed against soft cancellous bone increasing the risk of implant subsidence.

The second traditional end-plate preparation method preserves the end-plates by just removing cartilage with curettes. The end-plates are concave; hence, if a flat implant is used, the interface will not be well matched and the implant may not be very stable. Even if a convex implant is used, it is very difficult to match the implant geometry with the end-plate geometry, as the end-plate geometry varies from patient-to-patient and on the extent of disease.

The third but lesser used, traditional end-plate preparation method uses threaded fusion cages. The cages are implanted by burring out corresponding threads in the end-plates. This method also violates the structure.

2. Implant Retention

Traditional implants can migrate and expel out of the intervertebral body space following the path through which the implant was inserted. Typical implants are either threaded into place or have large "teeth" designed to prevent expulsion. Both options can create localized stress risers in the end-plates, increasing the chances of subsidence. The challenge of preventing implant expulsion is especially acute for PEEK implants, because the surface texture of PEEK is very smooth and slippery, with reduced purchase on the adjacent vertebrae.

3. Implant Subsidence

Subsidence of the implant is a complex issue and has been attributed to many factors. Some of these factors include aggressive removal of the endplate; an implant stiffness significantly greater than the vertebral bone; smaller sized implants which tend to sit in the center of the disc space against the weakest region of the end-plates; and implants with sharp edges which can cause localized stress fractures in the end-plates at the point of contact. The most common solution to the problem of subsidence is to choose a less stiff implant material. This is why PEEK and cadaver bone have become the most common materials for spinal fusion implants. PEEK is less stiff than cortical bone, but more stiff than cancellous bone. PEEK is a preferred choice for loading bone graft within an implant. In accordance with Wolfe's Law, the bone graft within the implant should be loaded in order for it to convert to living bone tissue. Living bone bridging from one vertebral body through the spacer and joining with the second vertebral body is the definition of "interbody fusion" which is one the primary goals of an ACDF procedure.

4. Bone Graft Volume

Cadaver bone implants are restricted in their size by the bone from which they are machined. Their wall thickness also must be great to create sufficient structural integrity for their desired clinical application. These design restrictions do not leave much room for filling the bone graft material into cortical bone implants. The exposure-driven limitations on implant size narrow the room left inside the implant geometry for bone grafting even for metal implants. Such room is further reduced in the case of PEEK implants because their wall thickness needs to be greater compared to metal implants due to structural integrity requirements.

5. Incorporation with Vertebral Bone

In many cases, the typical interbody fusion implant is not able to incorporate with the vertebral bone, even years after implantation. Such inability persists despite the use of a variety of different materials to construct the implants. PEEK has been reported to become surrounded by fibrous tissue which precludes it from incorporating with surrounding bone. Stiff, typically metallic, implants stress shield the bone graft and do not supports its transformation into living bone. In some designs of metal implants, such as those made of commercially pure titanium and titanium alloy, or tantalum and tantalum alloys, have surfaces that allow for bone ingrowth or on-growth and in some case even stimulate bone formation.

6. Limitations on Radiographic Visualization

For implants made of metal, the metal limits adequate radiographic visualization of the bone graft. Hence it can be difficult to assess fusion, if it is intended to take place. PEEK is radiolucent, so traditional implants made of PEEK need to have radiographic markers embedded into the implants so that implant position can be tracked on an X-ray. Cadaver bone has some radiopacity and does not interfere with radiographic assessment as much as metal implants. Metal implants are dense and inhibit the assessment of boney fusion via x-ray techniques. In addition, they can create significant artifacts when utilizing MRI or CT scans to post-operatively visualize the implant/bone interfaces.

Therefore, a need exists for improvements to interbody implants and the present technology is directed to cure such need.

SUMMARY OF THE INVENTION

The various systems and methods of the present technology have been developed in response to the present state of the art, and in response to the problems and needs in the art that have not yet been fully solved by currently available implants. The systems and methods of the present technology may provide a solution which eases end plate preparation, reduces implant expulsion, improving implant retention, reduces subsidence, allows increased room for bone graft and supports/stimulates bone graft incorporation/fusion, and improves radiographic visualization.

To achieve the foregoing, and in accordance with the technology as embodied and broadly described herein and given the need for an improved interbody spacer implant, this disclosure encompasses improved spinal fusion devices and procedures. In accordance with the disclosure, an interbody spacer implant comprises a body having a generally central axis and a centralized aperture extending through the body near the centralized axis. The body includes a first side having a perimeter and defining a first plane with an opposed second side having a perimeter and defining a second plane. The first side perimeter is connected at a first edge with a perimeter wall and the second side perimeter is connected at a second edge with the perimeter wall. The perimeter wall separates the first side and the second side. The first side further includes at least one lobe extending from the first perimeter toward the generally central axis. The intervertebral spacer implant wherein the at least one lobe may have a base adjacent the perimeter and an end region extending away from the base to a terminus. The base may have a first width and the end region a second width, wherein the first width is greater than that the second width. The base may have a first thickness and the end region a second thickness, wherein the first thickness is greater than the second thickness. The at least one lobe may include a plurality of lobes arranged around the first side perimeter. Each of the plurality of lobes may have a base adjacent the perimeter and an end region extending away from the base to a terminus, and wherein the termini are positioned about the generally central axis. The at least one lobe may extend outward from the first plane. The base may be substantially within the first plane and the end region extends outward from the first plane. The end region may be adapted to contact a first vertebral surface prior to the base or the first edge contacts the first vertebral surface. The end region may be adapted to flex toward the first plane when the implant is implanted between first and second vertebral bodies and the end region is adapted to have an anti-rotation or anti-movement function when engaged to the first vertebral surface. The at least one lobe may be a cantilever, including a base adjacent the first perimeter, an end region and a terminus. The at least one lobe may be adapted to function as a cantilever when the intervertebral spacer is implanted adjacent a vertebral body, the end region engages the vertebral body before the base or the perimeter, and wherein when the end region engages the vertebral body, the lobe is configured to flex toward the first plane.

In accordance with the disclosure, an intervertebral spacer implant includes a body including a generally central axis and a centralized aperture extending through the body along the generally central axis. The body may further include a first side having a perimeter and defining a first plane, an opposed second side having a perimeter and defining a second plane. The first side perimeter connected at a first edge with a perimeter wall. The second side perimeter connected at a second edge with the perimeter wall, wherein the perimeter wall separates the first side and the second side. The first side further includes at least one lobe extending from the first perimeter into the centralized aperture, toward the generally central axis. The intervertebral spacer implant may further include a first configuration and a second configuration wherein the implant is configured to change from the first configuration to the second configuration during or after implantation, or as fusion occurs, between adjacent vertebral bodies. In the first configuration, the at least one lobe on the first side may extend out of the first plane as the lobe extends from the first perimeter toward the generally central axis and the at least one lobe on the second side may extend out of the second plane as the lobe extends from the second perimeter toward the generally central axis. In the second configuration the at least one lobe of the first side may flex or displace toward the central plane and the at least one lobe of the second side may flex or displace toward the central plane. In the second configuration the first edge and the second edge are configured to disperse a load onto a rim of the first or second vertebral body, respectively. The at least one lobe on the first side may include a first gripper having a gripper base on the lobe and a gripper terminus extending from the base. When changing into the second configuration, the gripper terminus may rotate away from the first edge toward the generally central axis. The intervertebral spacer implant may include a first plow edge near the first edge and a second plow edge near the perimeter wall. The first plow edge and the second plow edge may be separated by a recess.

In accordance with the disclosure, an intervertebral spacer may include a first surface and a second surface connected and separated by a perimeter wall. The first surface may include at least one extension having a first region and a second region. The first region may be adjacent to the perimeter and the second region may extend away from the perimeter. When the implant is implanted adjacent to a vertebral body, the second region is configured to engage the vertebral body before the first region. The first region is capable of transitioning toward the second surface and the second region is capable of transitioning toward the second surface. The first region may require more force to transition than the second region.

In accordance with the disclosure, a method of fusing first and second adjacent vertebral bodies, wherein each vertebral body has endplates facing or opposing one another, includes inserting a spinal spacer into an intervertebral space between the first and second vertebral bodies. The implant is inserted adjacent the concave endplates on the first and second vertebral bodies. The implant includes a body having a generally central axis and a centralized aperture extending through the body near the centralized aperture. The body includes a first side having a perimeter and defining a first plane with an opposed second side having a perimeter and defining a second plane. The first side perimeter is connected at a first edge with a perimeter wall and the second side perimeter is connected at a second edge with the perimeter wall. The perimeter wall separates the first side and the second side. The first side further includes at least one lobe extending from the first perimeter toward the generally central axis. The method includes a step for allowing the first and second vertebral bodies to converge creating a load on the implant. The at least one lobe engages with one of the concave endplates so that the at least one lobe flexes to a degree commensurate with the increasing load. The method further includes that the implant is in a first native state prior to inserting between the first and second vertebral bodies. The implant transitions to a second loaded state after the first and second vertebral bodies are allowed to converge. In the second loaded state, the at least one lobe is flexed toward a central plane in the implant. The at least one lobe further includes a base adjacent the perimeter, an end region, and a terminus. When the implant transitions to the second loaded state, the base, the end region, and the terminus move relative to one another.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the invention's scope, the exemplary embodiments of the technology will be described with additional specificity and detail through use of the accompanying drawings in which:

FIG. 7A is a top view of yet another intervertebral spacer implant; FIG. 7B is an oblique view of the implant of FIG. 7A; FIG. 7C is a front view of the implant of FIG. 7A; FIG. 7D is a right view of the implant of FIG. 7A; FIG. 7E is another oblique view of the implant of FIG. 7A, from a different direction; and FIG. 7F is a back view of the implant of FIG. 7A;

FIG. 9A is a top view of yet another intervertebral spacer implant; FIG. 9B is an oblique view of the implant of FIG. 9A; FIG. 9C is a front view of the implant of FIG. 9A; FIG. 9D is a right view of the implant of FIG. 9A; FIG. 9E is another oblique view of the implant of FIG. 9A, from a different direction; and FIG. 9F is a back view of the implant of FIG. 9A;

FIG. 11A is a top view of yet another intervertebral spacer implant; FIG. 11B is an oblique view of the implant of FIG. 11A; FIG. 11C is a front view of the implant of FIG. 11A; FIG. 11D is a right view of the implant of FIG. 11A; FIG. 11E is another oblique view of the implant of FIG. 11A, from a different direction; and FIG. 11F is a back view of the implant of FIG. 11A;

DETAILED DESCRIPTION

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The term "adjacent" refers to items that are physically near or next to one another and may or may not be in physical contact. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard anatomical reference planes and spinal terminology are used in this specification with their customary meanings.

Figure 1:
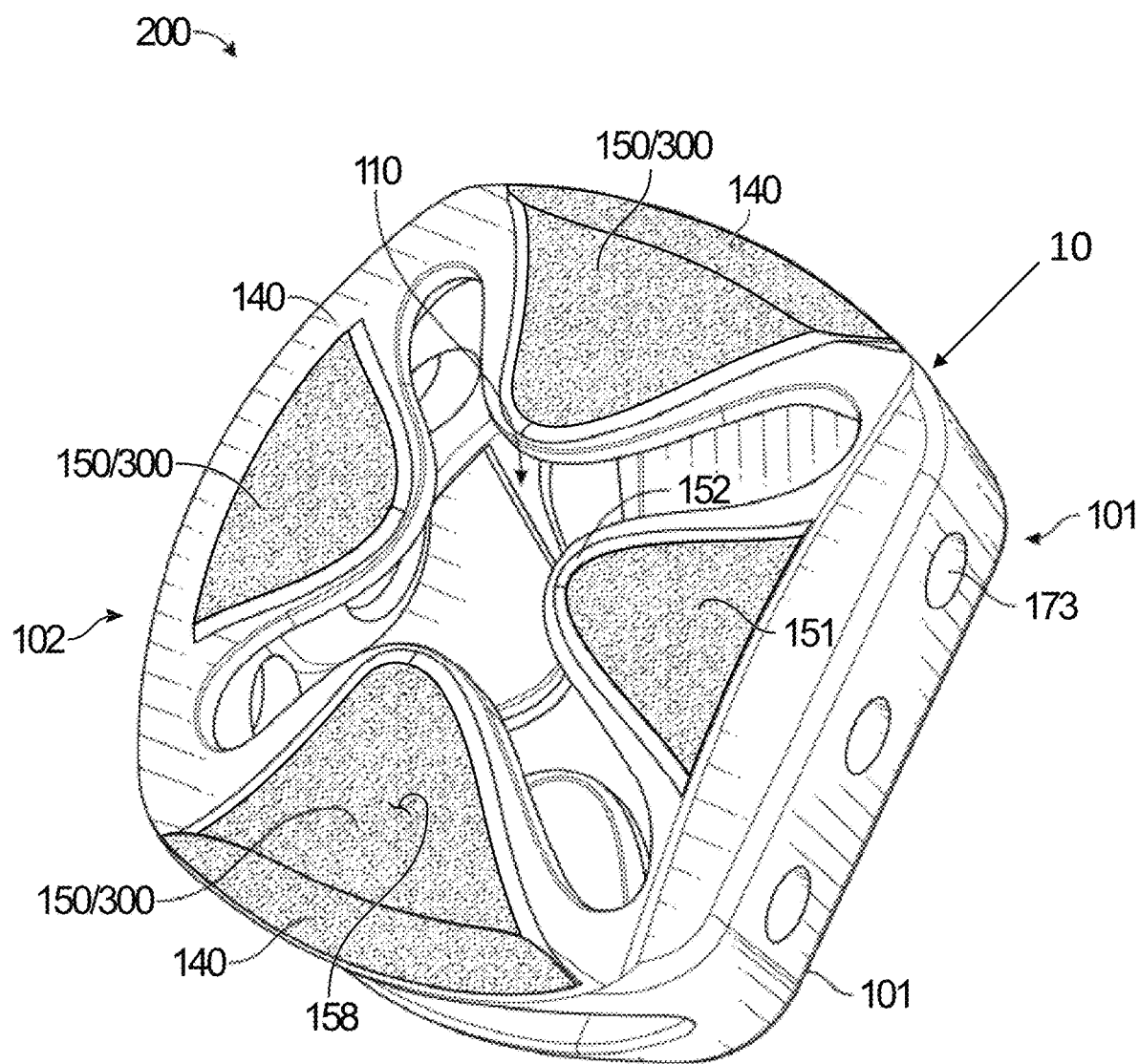
FIG. 1 is a perspective view of an intervertebral spacer implant.
Figure 2A:
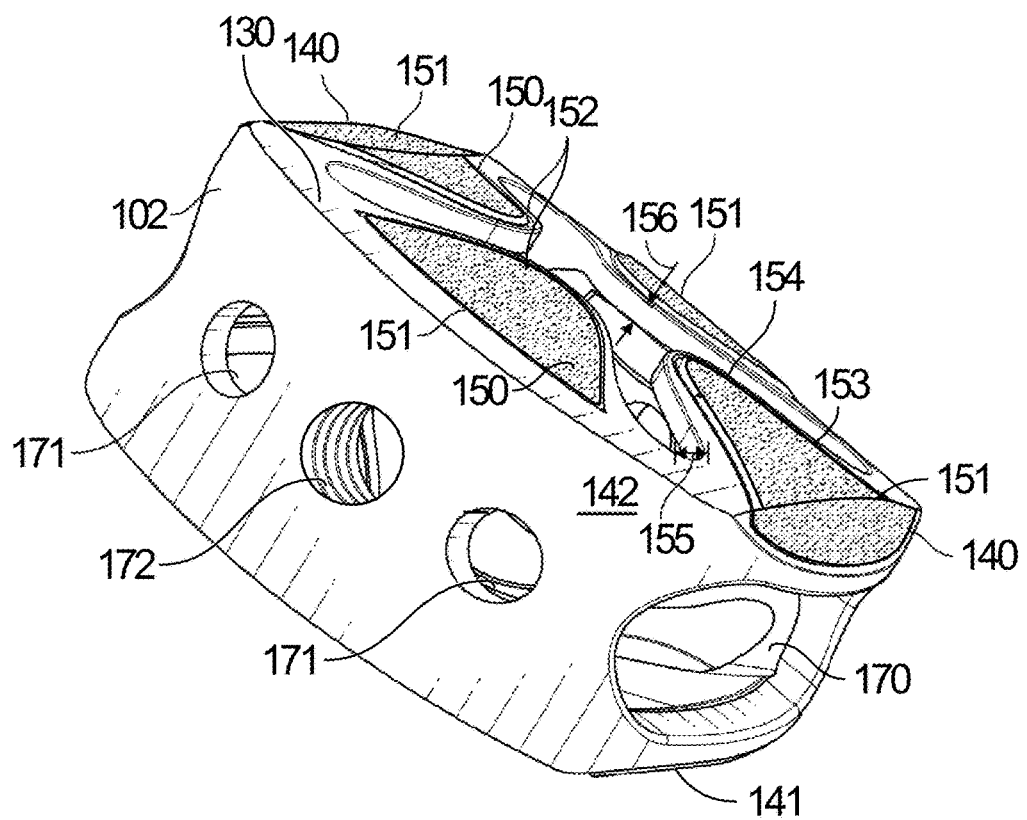
FIG. 2A is a front perspective view of the implant of FIG. 1.
Figure 2B:
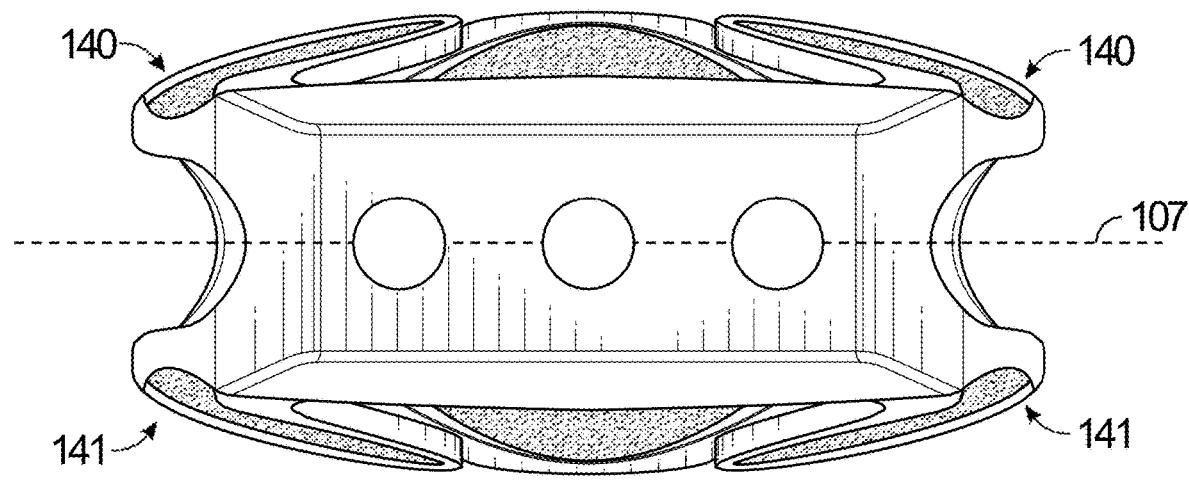
FIG. 2B is a front plan view of the implant of FIG. 1.
Figure 3:
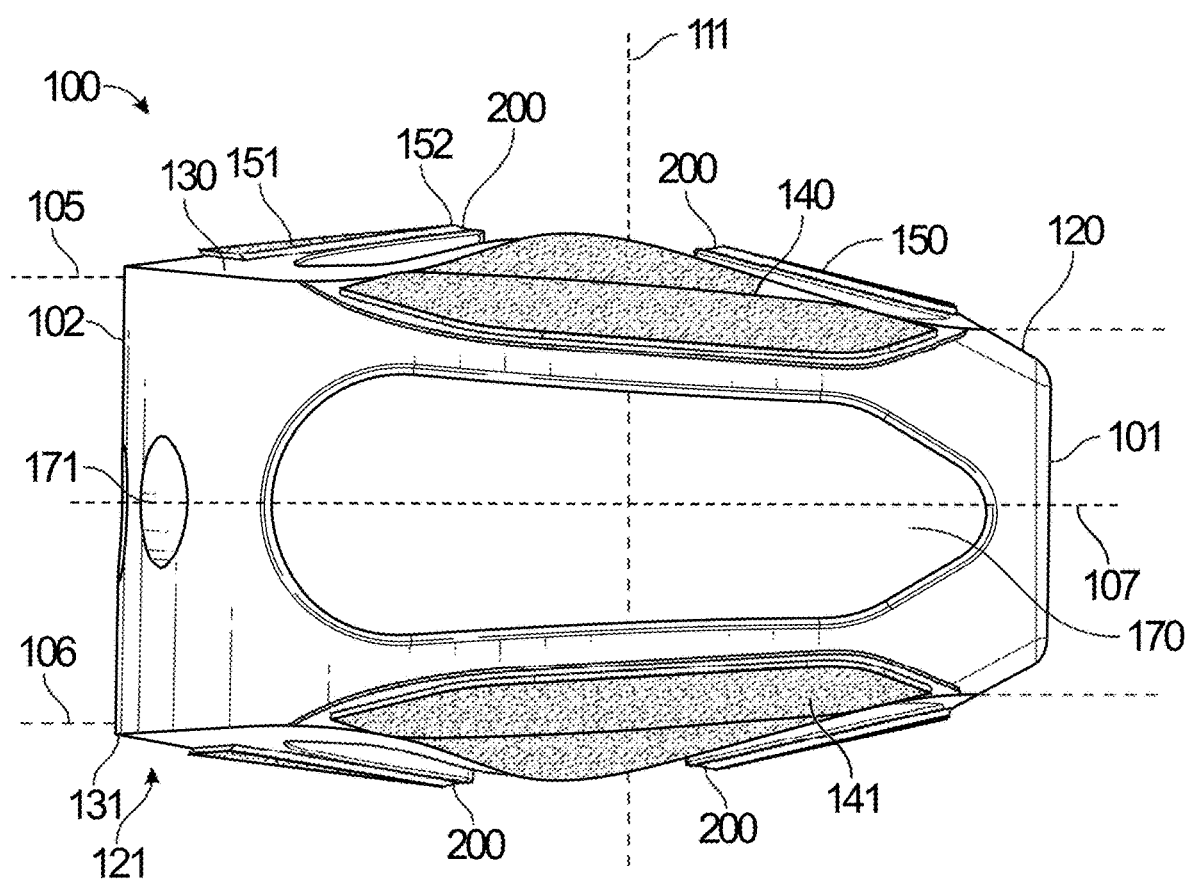
FIG. 3 is a right side plan view of the implant of FIG. 1.

FIGS. 1-3 illustrate, by way of example only, an intervertebral spacer implant 10 for performing an interbody fusion between adjacent vertebral bodies. The implant includes a body 100 with the dimensions of height, width, and length suitable for placement between vertebral bodies. In this example, the height extends along a cephalad-caudal direction, the width extends along a right-left direction, and the length extends along an anterior-posterior direction. The intervertebral spacer implant 10 may be made of any suitable biocompatible material. Various biocompatible materials contemplated include, but are not limited to, poly-ether-ether-ketone (PEEK), other polymers including bioresorbable polymers, ceramics, composites, bone or bone substitute materials, and biocompatible metals including stainless steel, titanium, or tantalum and their alloys. The implant 10 may also include multiple and combinations of the materials. The implant 10 may be manufactured by known methods such as machining, molding, forming, or 3D printing. The implant 10 may be provided in any number of shapes or sizes depending on the specific surgical procedure, need, or patient anatomy. The implant 10 may contain separate radiographic markers of any size of shape suitable to facilitate effective and accurate visualization of implant placement, necessary depending on the base material of the implant.

The intervertebral spacer implant 10 includes a body 100 with a centralized aperture 110, which is approximately in the center of the body 100. The centralized aperture may be skewed away from an absolute center of the body 100. The centralized aperture 110 may be large enough so that the body 100 may be effectively hollow, or the centralized aperture 110 may be small, narrow, or effectively a divot or series of divots in the body 100, such that the centralized aperture 110 does not pass completely through the body 100. In this embodiment, the body 100 would not be hollow or empty. The centralized aperture 110 in any of the contemplated embodiments may allow for bone ingrowth, weight reduction, and space for lobe 150 displacement.

The body 100 includes a leading edge 101 and a trailing edge 102. In this embodiment, the leading edge 101 may be a posterior side and the trailing edge 102 may be an anterior side. The body 100 includes a first side 120 and a second side 121 opposite one another. The first side 120 may be considered the top or superior aspect of the spacer 100 and the second side 121 may be considered the bottom or inferior aspect of the spacer 100; however, the top and bottom may also be interchangeable. As shown in FIG. 3, the first side 120 generally falls within a first plane 105 and the second side 121 generally falls within a second plane 106. The first plane 105 and the second plane 106 may converge toward the leading end 101 as in FIG. 3, but they may also take other orientations such as parallel, divergent relative to the leading end 101, or convergent relative to other points relative to the perimeter wall 142. The body may also have a generally central plane 107 that passes through the implant 10. The central plane 107 may be approximately between the first plane 105 and the second plane 106, and may be generally parallel to the transverse anatomical reference plane. A generally central axis 111 passes through the body 100 through the generally centralized aperture 110 and through the first side 120 and the second side 121, as depicted in FIG. 3. The generally central axis 111 may pass through the absolute center of the body 100 or it may be offset or angled in any direction. The axis 111 may be generally parallel to the cephalad-caudal direction.

The first side 120 has a perimeter 130 around the first side 120. The second side 121 has a second perimeter 131 which extends generally around the second side 121. The body 100 has a perimeter wall 142 that extends generally around the body 100 of the implant 10. The first side 120 connects with, or intersects, the perimeter wall 142 at a first edge 140. The second side 121 connects with, or intersects, the perimeter wall 142 at a second edge 141. The first edge 140 and second edge 141 may be thin edges as depicted on the leading end 101 in FIG. 1 or a wider edge 140 and 141 as shown in FIG. 3, on a medial side of the body 100. The first edge 140 extends around the first perimeter 130 and the second edge 141 extends around the second perimeter 131. The edges 140, 141, as well as the general shape of the body, increases stability of the implant after implantation. The shape and edges 140, 141 also reduce friction and drag during implantation. As shown in FIG. 2B, the edges 140, 141 are angled slightly below the outer first 105 and second 106 planes. The first and second edges 140, 141 face away from the body 100 and are configured to engage the rim of adjacent vertebral bodies. Depending on the load placed on the implant 10 by the adjacent vertebral bodies, the first and second edges 140, 141 may bear a substantial amount of the load, which then is dispersed on the rim of the vertebral bodies, rather than the softer central portion of the end plate.

The perimeter wall 142 may be uninterrupted or may have any number of apertures. FIG. 1 depicts side apertures on the sides of the perimeter wall 142. The side apertures 170 may be in communication with the centralized aperture 110 and may allow for bone growth into and through the body 100. The side apertures may also allow for radiographic visualization of bone healing. Alternatively, the side apertures 170 may not pass fully through the body 100. The side apertures 170 may also be contemplated as indentations or divots into the sides of the body 100. The perimeter wall may have other apertures 173 around the body 100, usually on the leading edge of the implant 10. As best viewed in FIGS. 2A and 2B, the body 100 may have any number of suitable features such as recesses, holes, notches and the like for engaging an insertion instrument (not shown) without deviating from the scope of the implant 10. One engagement feature is a threaded receiving aperture 172 in the perimeter wall 142 on the trailing end 102. The threaded receiving aperture 172 is dimensioned and configured to threadably receive a threaded portion of an insertion instrument. The threaded receiving aperture 172 may extend inwardly toward the generally central axis 111. In addition to, or replacing, the generally threaded receiving aperture 172, the perimeter wall 142 may have guide apertures 171. FIG. 2A depicts a pair of guide apertures 171 flanking the threaded receiving aperture 172. The aperture 172 may also be unthreaded. The guide apertures 171 may function as a support or guide feature for an insertion instrument (not shown) or they may function as another route for bone ingrowth. The guide apertures 171 allow the threaded connection to fixate the insertion instrument to the spacer and allow for positioning of the implant. An inserter with pins, which engage the guide apertures 171, may torque the implant about an axis through the threaded aperture 172. Any of the apertures or divots of the implant 10 may have varying shapes, sizes, and orientations, which may be suitable for the surgical implantation of the implant 10. Additionally, these features may be used for implant repositioning and or removal if required.

As shown in FIG. 1, the first side 120 has at least one lobe 150 or extension, which may be likened to a cantilever 300. A cantilever is a structural element anchored at one end to a support, from which it protrudes. When subjected to a structural load, the cantilever carries the load to the support. The lobe is structured to extend from a base 151 to an end or first region 158 and end at a terminus 152 or second region. The base 151 is adjacent to the first perimeter 130. The end region 158 extends away from the base 151 and the first perimeter 130 and toward the generally central axis 111. As shown in FIG. 2A, the lobe 150 has a first width 153 at the base 151 and a second width 154 at the terminus 152. The width decreases along the end region 158 to the terminus 152, so that the first width 153 is greater than the second width 154. The lobes 150 depicted in the figures have a generally curved and convex shape, but it is envisioned that the lobes 150 can have other suitable shapes, such as a terminus 152, with a width greater than or equal to the base 151, or a terminus 152 equal in width to the base 151. Other shapes of the end region 158 are contemplated to include different transitions from the base 151 to the terminus 152, including symmetrical, asymmetrical, acute, obtuse, or other suitable means. The at least one lobe 150 may be have a convex shape that complements the concave shape of the end plate, along the cephalad or caudal surface.

As shown in FIG. 2, the lobe 150 has a first thickness 155 at the base 151 and a second thickness 156 at the terminus 152. The first thickness 155 is greater than the second thickness 156. The thickness decreases along the end region 158 to the terminus 152. The lobe 150 depicted in the figures have a generally curved shape, but it is envisioned that the lobes 150 have other suitable shapes, such as a terminus 152 with a width greater than or equal to the base 151, or a terminus 152 equal in width to the base 151. Other shapes of the end region 158 are contemplated to include different transitions from the base 151 to the terminus 152, including symmetrical, asymmetrical, acute, obtuse, or other suitable means.

In addition to having at least one lobe 150, the implant may have a plurality of lobes 200 about the generally central axis, as shown in FIGS. 1-3. Furthermore, the at least one lobe 150 or the plurality of lobes 200 may be present on both the first side 120 and the second side 121. Any number or arrangement of the lobes 150/200 are contemplated in order to address patients' needs and anatomy. As shown in FIG. 3, in a side plan view, the body 100 has first 105 and second planes 106. The plurality of lobes 200 are present on both the first side 120 and the second side 121. As depicted in FIG. 3, the lobe 150 curves or arcs away from the centralized aperture 110 and outward from the first plane 105. The same orientation and juxtaposition may exist on the second side.

The at least one lobe 150 and the plurality of lobes 200 may have a convex profile, which may be complementary to a concave nature of vertebral endplates. With respect to the first side 120, the base 151 of the lobe 150 as well as the first perimeter 130 and the adjacent first edge 140 may exist within the first plane 105. The first edge 140 may also be slightly below the first plane 105, toward the central plane 107, as shown in FIG. 2B. Extending from the base 151, the end region 158 extends outward from the first plane 105. The terminus 152 may be outside, aligned with, or inside the first plane 105. This same arrangement or orientation may exist for the second side 121 and the second plane 106. The second edge 141 may exist within the second plane 106, or in a directly toward the central plane 107, as shown in FIG. 2B.

The end region 158 of at least one lobe 150, or of the plurality of lobes 200, is configured to engage vertebral bodies adjoining the target disc space. In the embodiment depicted in FIGS. 1-3 show a plurality 200 of lobes 150 on both the first side 120 and the second side 121. In this embodiment, the end region 158 of each of the lobes 150, extend out of the first 105 and second 106 planes. With this embodiment, the implant 10 is configured so that when the implant 10 is positioned between adjacent vertebrae, the end regions 158 contact the surface of the vertebral bodies prior to the vertebral body contacting any other portion of the implant 10 body 100. With increased load on the end regions 158 from the vertebrae on the implant 10, the lobes 150 are capable to flex or bend to absorb or cushion the load on the implant 10. As the end regions 158 receive the load from the adjacent vertebrae, the lobe flexes toward the respective first 105 and/or second 106 planes, respectively, and toward the central plane 107. The terminus 152 may flex into the centralized aperture 110 as the lobe 150 flexes. Any portion of the lobe 150 may flex past the first 105 and second 106 planes and continue toward the central plane 107. The flexibility of the at least one lobe 150 or the plurality of lobes allows the profile of the implant to complement a vertebral endplate that is not fully concave.

The shape of the lobe 150 and the end region 158 may be oriented so that the end region 158 engages the vertebral body closer to the apophyseal rim, containing cortical bone, rather than the soft central cancellous bone. In an embodiment with four lobes 150 on each side 120 121, the load from the adjacent vertebral bodies may be distributed about the eight total lobes. The dimensions of the lobes 150 having a first thickness 155 greater than the second thickness 156, allows the end region 158 and the lobe to flex in a non-linear fashion or relative motion. A middle portion of the end region 158 and extending toward the terminus 152 would flex more easily than the lobe nearer the base 151. By spreading the load of adjacent vertebral bodies across at least one lobe 150 in the implant, and preferably a plurality of lobes 200, the implant 10 reduces the risk of subsidence into the vertebrae and the cancellous bone, by increasing the contact area between the bone and the implant. The overall force against a localized point on the vertebral endplate is spread, and as the lobe flexes, the contact point between the end region 158 and the vertebra is shifted toward the harder cortical bone at the apophyseal rim, supported by the first edge 140 and the second edge 141. As the load from the adjacent vertebra increase, the lobes 150 deflect further, and it is possible for the entire load to be supported at the perimeter 130 and the edges 140, 141 and on the perimeter wall 142. Any lobe 150 or combination of lobes 150, 200, may include surface features that encourage bone ingrowth. The features may include pores, ridges, loops, holes, spaces, grooves, or any known surface that increases purchase or grips on the adjacent bone. As the spacer has been packed with cancellous bone graft when the first and second surfaces deflect they cause the bone graft to support some of the load being transmitted from the adjacent vertebra. In some embodiments, the stiffness of the first and second sides 120, 121, in compression along the axis 111 generally parallel with the perimeter wall, is equal to or less than the compressive modulus of cancellous bone. In accordance with structural mechanics, this situation allows the bone graft to support a significant portion of the spinal load and in accordance with Wolfe's Law facilitates its incorporation into the fusion mass.

Figure 4:
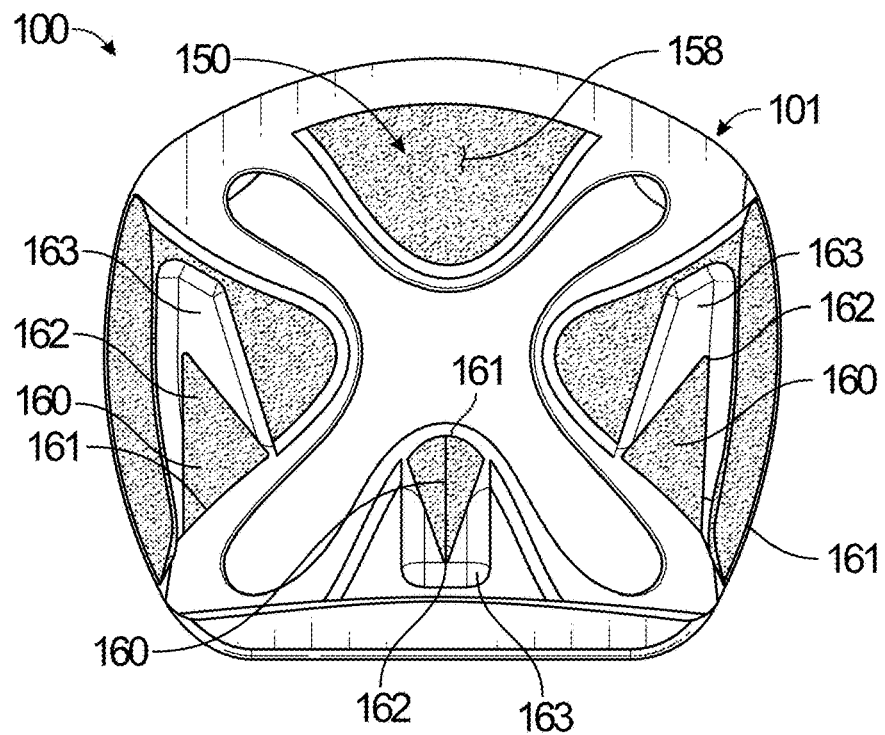
FIG. 4 is a top plan view of another intervertebral spacer implant.
Figure 5:
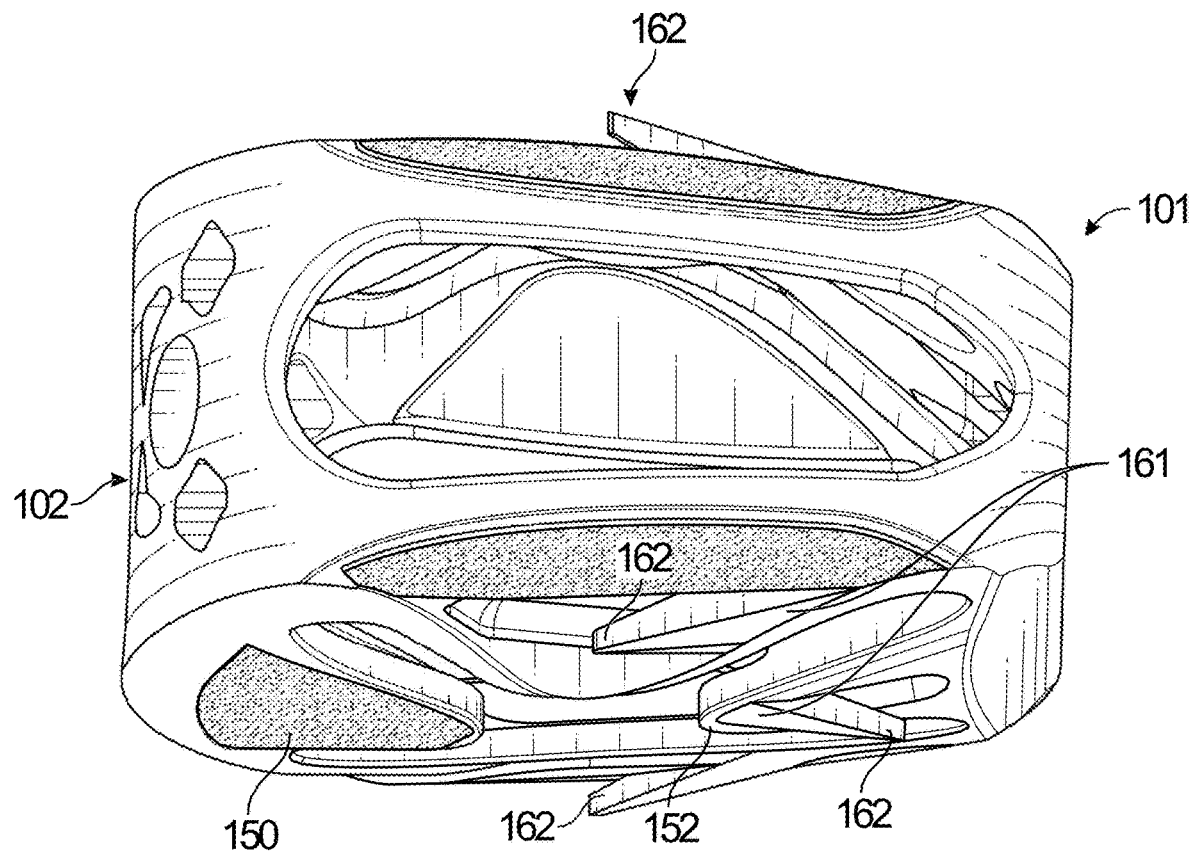
FIG. 5 is a side perspective view of the implant of FIG. 4.
Figure 6:
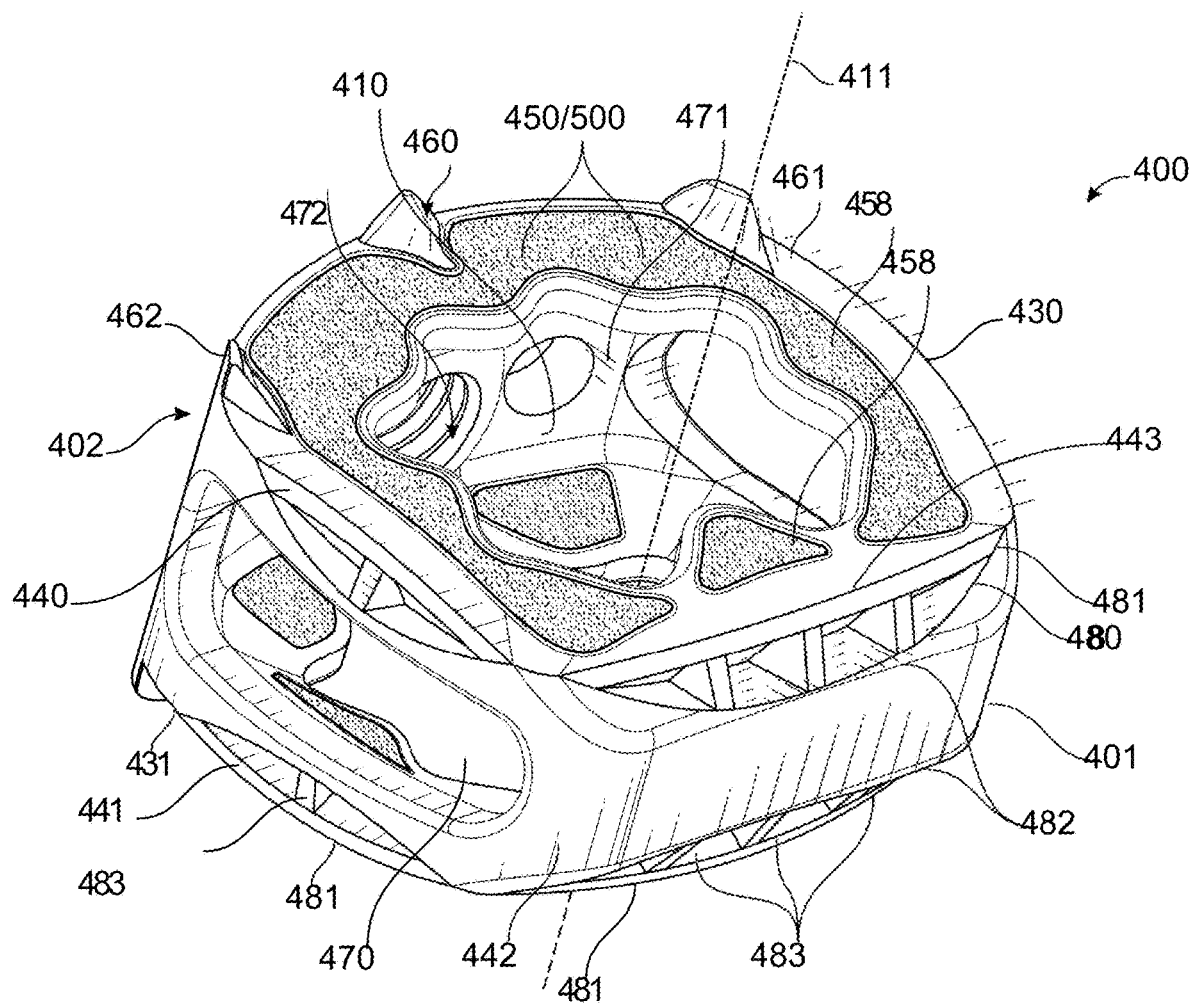
FIG. 6 is a top perspective view of yet another intervertebral spacer implant.
Figure 8A:
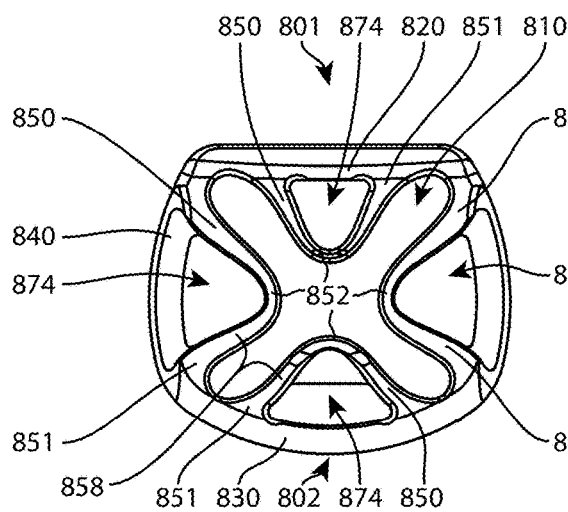
FIG. 8A is a top view of yet another intervertebral spacer implant.
Figure 8B:
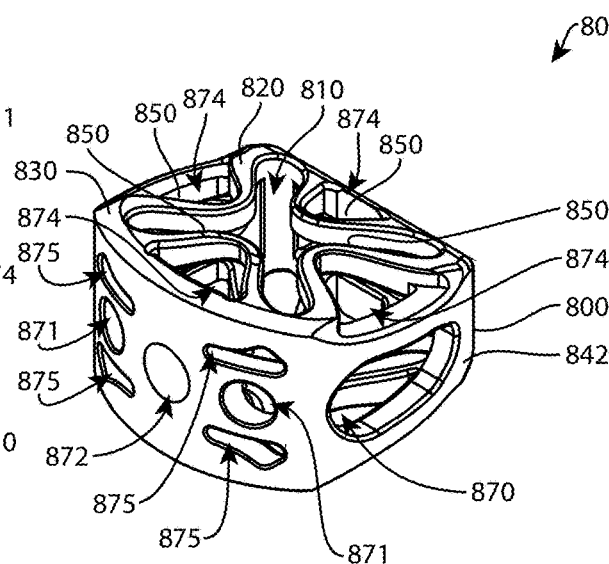
FIG. 8B is an oblique view of the implant of FIG. 8A.
Figure 8C:
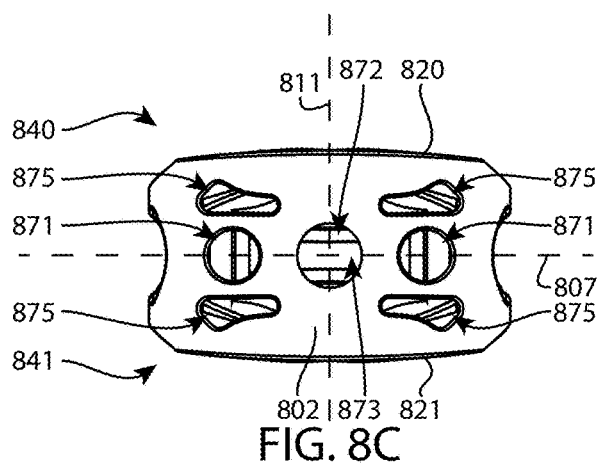
FIG. 8C is a front view of the implant of FIG. 8A.
Figure 8D:
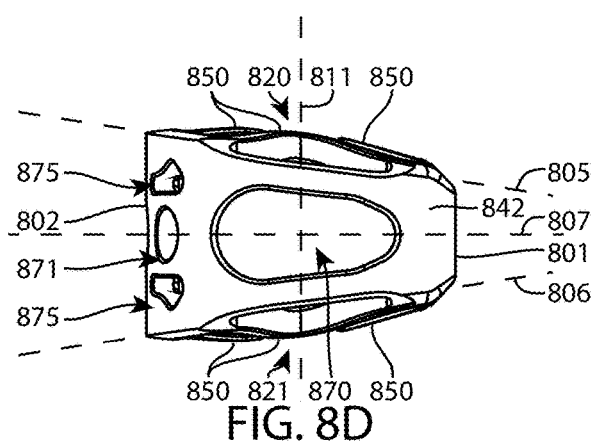
FIG. 8D is a right view of the implant of FIG. 8A.
Figure 8E:
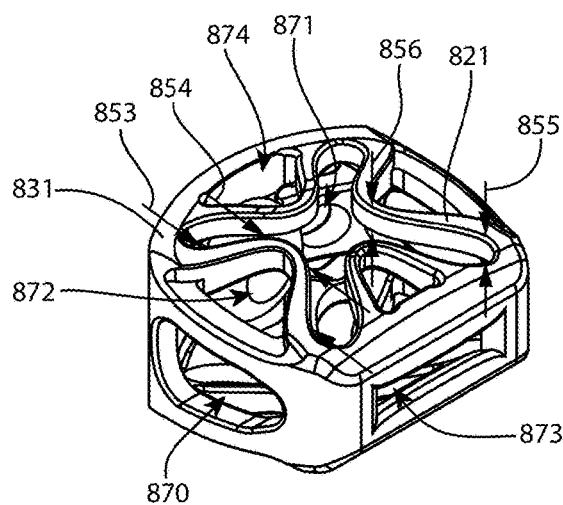
FIG. 8E is another oblique view of the implant of FIG. 8A, from a different direction.
Figure 8F:
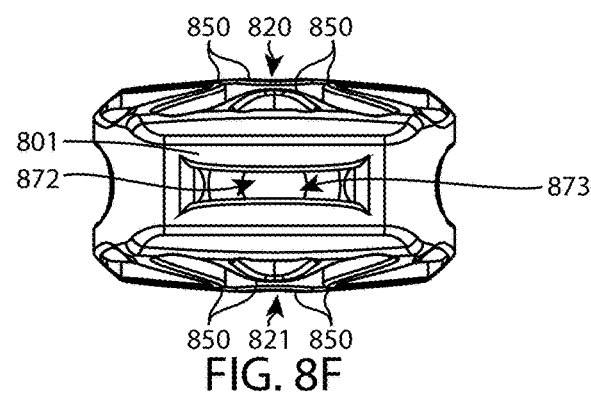
FIG. 8F is a back view of the implant of FIG. 8A.
Figure 10A:
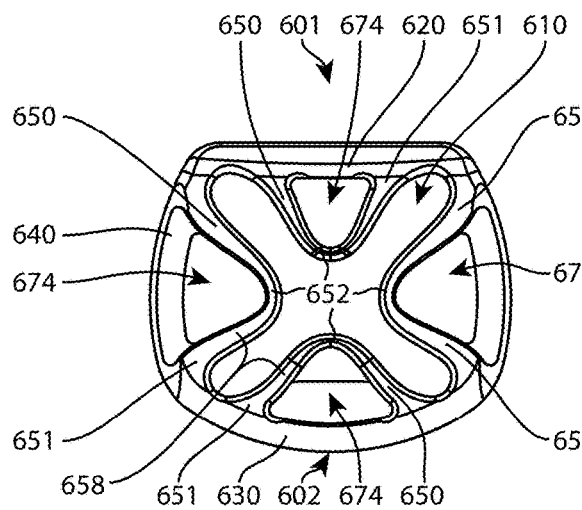
FIG. 10A is a top view of yet another intervertebral spacer implant.
Figure 10B:
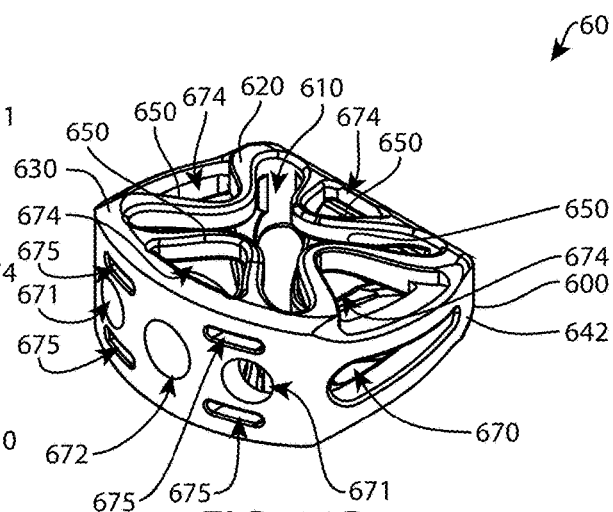
FIG. 10B is an oblique view of the implant of FIG. 10A.
Figure 10C:
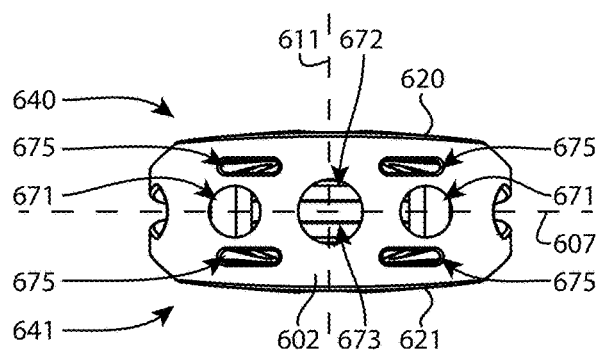
FIG. 10C is a front view of the implant of FIG. 10A.
Figure 10D:
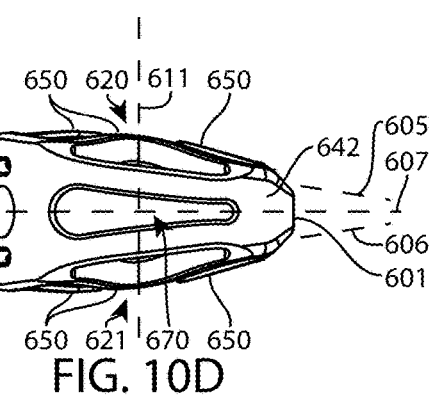
FIG. 10D is a right view of the implant of FIG. 10A.
Figure 10E:
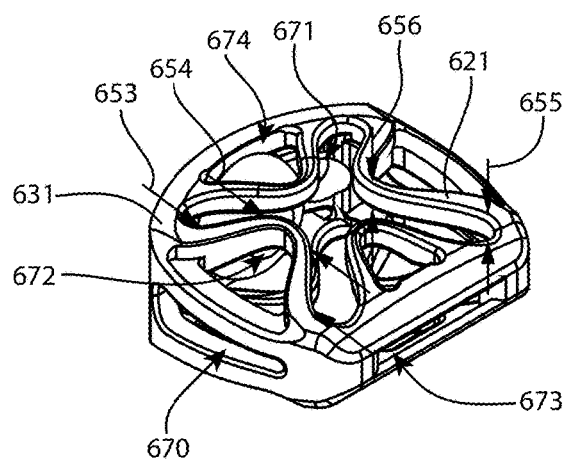
FIG. 10E is another oblique view of the implant of FIG. 10A, from a different direction.
Figure 10F:
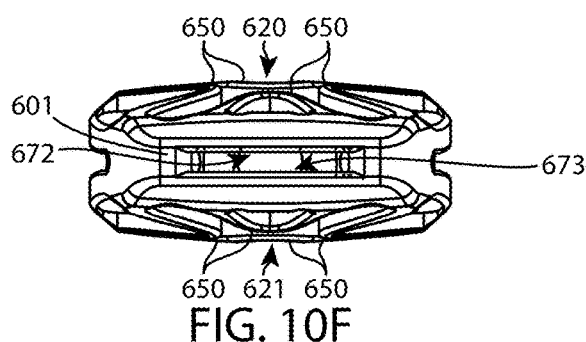
FIG. 10F is a back view of the implant of FIG. 10A.

The implant 10 may include a plurality of anti-migration features designed to increase the friction between the implant and the adjacent contacting surfaces of the vertebral bodies. Such anti-migration features may include ridges, teeth, lugs, or other purchase-inducing surface treatments. The anti-migration features also stabilize the implant by resisting torsional loads, which might inhibit fusion. As shown in an embodiment of FIGS. 4 and 5, the implant 10 has grippers 160 functioning as an anti-migration feature. These grippers may be located on a lobe 150 in an area of the end region 158 that is configured to engage adjacent vertebral bodies. FIG. 4 shows the grippers 160 aligned generally parallel with the leading and trailing ends 101, 102, which may commonly be an anterior-posterior orientation. The grippers may be oriented so that the termini 162 are directed in the same direction, or as shown in FIGS. 5 and 6, the implant 10 may have multiple grippers on the leading end 101 of the implant body 110, wherein the gripper termini 162 are oriented in opposite directions. This orientation allows for better prevention of anterior-posterior expulsion as well as inhibit lift off from the bone during bending motions. Each gripper 160 may have a gripper base 161 located on the lobe 150, preferably on the end region 158, and a gripper terminus 162. The gripper terminus may have a pointed or other engaging geometry to encourage efficient purchase on the vertebral body. The gripper 160 in FIG. 4 has a triangular shape with a relatively pointed or sharp gripper terminus 162. Each lobe 150 with a gripper 160 may include a divot 163 in the respective lobe 150, beneath the gripper 160. The divot 163 is configured to accommodate and to allow the gripper 160 to flex into the lobe 150 when the load from the vertebral bodies are transferred to the implant 10. Open space between the gripper 160 and the divot may also allow for bone ingrowth and facilitate better implant stabilization. The grippers 160 may also be rigid without substantial flexing and may allow for penetration of the vertebral endplate. Penetration of the endplate may allow blood to flow from the cancellous portion of the vertebral body. FIG. 5 demonstrates grippers 160 on both the first side 120 and the second side 121 of the implant 10. The gripper terminus 162 may further extend past the outer most part of the end region 158 or the terminus 152 of the lobe 150.

The implant 10 may have a first and second configuration. In the first configuration, the implant is in a relaxed state, in which the lobes are generally extending out of the first and second planes 105, 106, as generally shown in FIGS. 1-5. The end regions 158, as well as any gripper 160, are outside of the planes 105 106 and the edges are either in plane or slightly inward of the planes 105 106, toward the centralized aperture. The second configuration is a transitioned state, realized when a load has been placed on the implant 10. The second configuration may also be referred to as a deflected state. In practice, the second configuration occurs after implantation of the implant 10 between two adjacent vertebrae, and the vertebrae are allowed to apply a load on both the first side 120 and the second side 121 of the implant body 100. As the load increase on the implant body 100, the end regions 158 on at least one lobe 150 or a plurality of lobes 200, accept the load. Each lobe 150 responds to the load and flexes inwardly toward the centralized aperture 110 and the central plane 107. If the lobes contain grippers 160, the grippers 160 engage and bite into the end plates. The grippers then flex inwardly toward the divots 163, to a maximum, then the lobe 150 flexes toward the centralized aperture 110. As the load increases, each lobe 150 may flex, and because the end region 158 has a curvature, the point of contact with the end plate may shift in the direction toward the perimeter 130, 131, and thus closer to the rim of the vertebral body. Once the load from the vertebral bodies has stabilized, and based on the patient's anatomy, each lobe 150 within the plurality 200 may have flexed by different amounts, to properly stabilize the spine. The lobes and/or grippers may flex elastically or plastically. Elastic deflection is temporary and the lobes and/or grippers return to the relaxed state when load is removed. Plastic deflection is substantially permanent and the lobes and/or grippers remain deformed when load is removed.

In the transition from the first configuration to the second configuration as the at least one lobe 150 flexes toward the central plane, it is foreseen that the first edge 140 and the second edge 141 receive an increase in the load applied by the adjacent first and second vertebral bodies. As discussed above, the load applied by the adjacent vertebral bodies may be dispersed by the first 140 and second 141 edges onto the outer rims of the endplates. The endplates are able to withstand a greater load than the central portion of the endplates and may rotate when the lobe 150 is flexed to a second configuration. The edge rotation may occur about an axis generally parallel to the base of a lobe 150. For example, if the first edge 140 is in or outward-from the first plane 105, when the lobe 150 is flexed toward the first plane 105, the first edge 140 will rotate up and outward from the first plane 105. If the first edge 140 is below or inward of the first plane 105, in the first configuration, when the lobe 150 is flexed to a second configuration, the first edge rotates about an axis parallel the base 151, both toward and outward the first plane 105. The movement of the edge away from the centralized aperture may create additional anti-migration features and functions of the implant 10. The same function may occur on the second side 121 of the implant with the second edge 141. The implant 10 may have any variation of edge geometries in the first configuration.

FIG. 6. shows an implant embodiment 40 having a plurality of lobes 500. Each lobe 450 has a generally triangular shape with a base 451 and a terminus 452, with an end region 458 therebetween. Each base 451 has a first width 453 and each terminus has a second width 454. The first width 453 is generally greater than the second width 454. The differences in width allow for a cantilever 600 function of each of the lobes 450, so that the end region can flex toward the centralized aperture when a load is placed on the implant 40. The implant body 400 has a leading end 401, a trailing end 402, with a centralized aperture 410, and a generally central axis 411. The implant 40 has a first side 420, a second side 421, with a first perimeter 430 and a second perimeter 431, respectively. The implant body 400 has at least a first edge 440 between the first perimeter 430 and a perimeter wall 442, as well as a second edge 441 between the second perimeter 431 and the perimeter wall 442. The body 400 may also have a plurality of apertures like a guide aperture 471, side apertures 470, and attachment apertures 472. The embodiment in FIG. 6 also has first and second plow edges 481, 482 separated by a recess 480. The first plow edge is adjacent to the first perimeter 430 and the second plow edge is adjacent the perimeter wall 442. The first plow edge 481, the second plow edge 482, and the recess 480 may extend around the whole perimeter 430, or may be broken up, as shown in FIG. 6. The same plow structure may be present on the second side 421. The first 481 and second 482 plow edges create additional grip and purchase on the rim of the adjacent vertebral bodies, when the implant 40 is implanted. The recess 480 and plow edge supports 483 allow for additional locations for stabilizing bone ingrowth. FIG. 6 depicts additional examples of gripper 460 shapes. Gripper 460 may have a base 461 located closer to the first 440 or second 441 edges or the base 451 of the lobe 450. The gripper 460 may have a terminus 462 oriented away from the first 420 or second sides 421.

The implant 10, 40 may be used in a method of fusing adjacent first and second vertebral bodies. In an exemplary method, the intervertebral space may be distracted prior to insertion of the implant 10, 40. Prior to insertion of the implant 10, 40, the intervertebral space is prepared. In a method of installation, a discectomy may be performed so that the disc is removed in its entirety. An alternative method may allow for only a portion of the disc to be removed. The endplates of the vertebral bodies may be scraped to expose suitable surfaces, which may bleed, and which may encourage bone ingrowth to the implant. Once the intervertebral space is sufficiently prepared, the implant 10, 40 may be introduced in a first relaxed state into the space and seated properly. The implant may be implanted via an endoscopic tube or other known implantation means.

After the implant 10, 40 is positioned, the adjacent vertebral bodies may be allowed to converge, putting a load onto the implant 10, 40. The concave endplates are allowed to engage the at least one lobe 150 or a plurality of lobes 200 on the implant 10, 40, which then flexes toward a central plane 107. The complementary shape of the lobes 150, 200 engage the endplates and assist in properly positioning and securing the implant 10, 40 in place. The implant 10, 40 may have grippers 160, 460 which further and more deeply engage the endplates to assist in keeping the implant in the intended location. The grippers 160, 460 may also encourage the endplates to bleed, encouraging bone ingrowth. As the load from the vertebral bodies increases, the at least one lobe 150 or the plurality of lobes on a first side 120 or on both the first 120 and second 121 sides of the implant act as a cantilever and flex toward a central plane. The implant 10, 40 transitions from the first relaxed state to a second loaded state, wherein the implant 10, 40 is taking on the full load from the adjacent vertebral bodies. During and after the transition to the second loaded state, the first 140 and second 141 edges may engage with the rim of the endplates and disperse the load across this stronger portion of the vertebral body.

FIGS. 7A-11F illustrate a set of implants 50, 60, 70, 80, 90, all shown at the same scale. Implant 90 of FIGS. 7A-F is a 9 mm size; implant 80 of FIGS. 8A-F is an 8 mm size; implant 70 of FIGS. 9A-F is a 7 mm size; implant 60 of FIGS. 10A-F is a 6 mm size; and implant 50 of FIGS. 11A-F is a 5 mm size. The implants each have the dimensions of height, width, and length suitable for placement between vertebral bodies. The height extends along a cephalad-caudal direction, the width extends along a right-left direction, and the length extends along an anterior-posterior direction. The implants may be made of any suitable biocompatible material. Various biocompatible materials contemplated include, but are not limited to, poly-ether-ether-ketone (PEEK), other polymers including bioresorbable polymers, ceramics, composites, bone or bone substitute materials, and biocompatible metals including stainless steel, titanium, or tantalum and their alloys. The implants may also include multiple materials and/or combinations of materials. The implants may be manufactured by known methods such as machining, molding, forming, or 3D printing. The implants may be provided in any number of shapes or sizes depending on the specific surgical procedure, need, or patient anatomy. The implants may contain separate radiographic markers of any size of shape suitable to facilitate effective and accurate visualization of implant placement, necessary depending on the base material of the implant.

Implants 50, 60, 70, 80, 90 illustrate principles for designing metal intervertebral spacer implants whose functional stiffness under normal in vivo load bearing conditions is equal to or less than the functional stiffness of conventional PEEK intervertebral spacer implants, which usually falls within the range of 5,000 N/mm to 20,000 N/mm. Implants 50, 60, 70, 80, 90 have been designed in titanium alloy for implantation into the cervical spine where normal in vivo load bearing conditions include axial (superior-inferior) compression loads that are less than 400 N, less than 200 N, or less than 130 N. The implants exhibit enhanced flexibility or reduced stiffness under axial compression loads from 0 N to 130 N, 0 N to 200 N, or 0 N to 400 N, despite titanium alloy having a Young's modulus that is much greater than PEEK. Implant stiffness under these axial compression loads may be less than or equal to 20,000 N/mm. Implant stiffness may be less than or equal to 15,000 N/mm, less than or equal to 10,000 N/mm, less than or equal to 5,000 N/mm, less than or equal to 4,000 N/mm, less than or equal to 3,000 N/mm, less than or equal to 2,000 N/mm, less than or equal to 1,000 N/mm, or less than or equal to 500 N/mm. The implants have also been designed to sustain axial compression loads equal to or greater than 1500 N. Under these higher loads, the implants exhibit higher stiffness because the loads are borne mainly by the perimeter wall. While this disclosure is made in the context of implants and loads for the cervical spine, the design principles are adaptable to implants and loads for the thoracic or lumbar spine.

The axial compressive stiffness of the implants disclosed herein is modulated by the lobes on the first and/or second sides of the implants. The lobes progressively deflect under load and thereby decrease the functional stiffness of the implants under normal in vivo loads versus conventional implant designs that have solid first and/or second sides or that lack compliant structures like the lobes. One principle illustrated by implants 50, 60, 70, 80, 90 is that all lobes share the in vivo load evenly. In other words, each lobe carries the same load, has the same deflection characteristics, has the same stiffness, and/or has the same contact area for a given load. One will appreciate that if the in vivo load is 400 N, and if the implant includes four lobes per side, then the load per lobe is 100N; alternatively, if the implant includes only two lobes per side, then the load per lobe would be 200N. However, implant design is multi-factorial and implant manufacturing necessarily involves numerous tolerances applied to a nominal design. The complete array of design constraints for a specific implant design may result in nominal lobes which carry approximately the same load and have approximately the same deflection characteristics. Each nominal lobe may be the same as every other nominal lobe within ±50% (i.e., lobe 2 is 50% to 150% of lobe 1). Preferably, each nominal lobe may be the same as every other nominal lobe within ±20%, within ±15%, within ±10%, or within ±5%.

The axial compressive stiffness of the implants 50, 60, 70, 80, 90 is further modulated by changing the bending stiffness of the perimeter walls. The bending stiffness of the perimeter walls may be reduced in the vicinity of the lobe bases as compared to solid, unmodified perimeter walls. Another principle illustrated by implants 50, 60, 70, 80, 90 is that the perimeter walls include features which contribute to all lobes sharing the load evenly. In other words, the perimeter wall in the vicinity of each lobe base is modified to adjust the load/deflection/stiffness of that lobe.

Referring to FIGS. 7A-F, implant 90 includes the following structures and/or features which may be as described above for implants 10, 40 and having related reference numbers: body 900, leading edge/end 901, trailing edge/end 902, first plane 905, second plane 906, central plane 907, centralized aperture 910, central axis 911, first side 920, second side 921, first perimeter 930, second perimeter 931, first edge 940, second edge 941, perimeter wall 942, lobe 950, lobe base 951, lobe terminus 952, lobe first width 953, lobe second width 954, lobe first thickness 955, lobe second thickness 956, lobe end region 958, side apertures 970, guide apertures 971, receiving/attachment aperture 972, and/or apertures 973. Implant 90 may optionally include one or more grippers, each with a gripper base and gripper terminus, each optionally associated with a divot, like gripper 160, 460, gripper base 161, 461, gripper terminus 162, 462, and divot 163 of implants 10, 40. The lobes 950 of implant 90 may include bone ingrowth and/or ongrowth features as depicted in FIGS. 1-6, such as pores, ridges, loops, holes, spaces, lobe apertures 974 as shown, grooves, or any known surface that increases purchase or grips on the adjacent bone. The lobe apertures 974 may be filled with porous material.

Implant 90 includes large side apertures 970 and a large aperture 973 in the leading end 901. These apertures 970, 973 reduce the bending stiffness of the perimeter wall 942 in the vicinity of the lobe bases 951 of the side and leading lobes 950 to increase the flexibility of the lobes. The trailing end 902 includes the receiving/attachment aperture 972 and the flanking guide apertures 971, as well as four more apertures 975 which are located in the vicinity of the lobe bases 951 of the trailing lobes 950. The apertures 971, 972, 975 may function together to reduce the bending stiffness of the perimeter wall 942 in the vicinity of the lobe bases 951 of the trailing lobes 950 to increase the flexibility of the lobes. Each aperture 975 is elongated along a side-to-side (right-left) direction. Preferably, the apertures 975 are enlarged toward their lateral (outboard) ends so that the enlargement coincides with each side of the lobe base 951. Preferably, the lateral ends of the apertures 975 are enlarged toward the first and second sides 920, 921, respectively as shown, again to coincide with each side of the lobe base 951. The illustrated apertures 975 represent one of a plurality of alternative aperture configurations for the 9 mm size implant 90.

Referring to FIGS. 8A-F, implant 80 includes the following structures and/or features which may be as described above for implants 10, 40 and having related reference numbers: body 800, leading edge/end 801, trailing edge/end 802, first plane 805, second plane 806, central plane 807, centralized aperture 810, central axis 811, first side 820, second side 821, first perimeter 830, second perimeter 831, first edge 840, second edge 841, perimeter wall 842, lobe 850, lobe base 851, lobe terminus 852, lobe first width 853, lobe second width 854, lobe first thickness 855, lobe second thickness 856, lobe end region 858, side apertures 870, guide apertures 871, receiving/attachment aperture 872, and/or apertures 873. Implant 80 may optionally include one or more grippers, each with a gripper base and gripper terminus, each optionally associated with a divot, like gripper 160, 460, gripper base 161, 461, gripper terminus 162, 462, and divot 163 of implants 10, 40. The lobes 850 of implant 80 may include bone ingrowth and/or ongrowth features as depicted in FIGS. 1-6, such as pores, ridges, loops, holes, spaces, lobe apertures 874 as shown, grooves, or any known surface that increases purchase or grips on the adjacent bone. The lobe apertures 874 may be filled with porous material.

Implant 80 includes large side apertures 870 and a large aperture 873 in the leading end 801. These apertures 870, 873 reduce the bending stiffness of the perimeter wall 842 in the vicinity of the lobe bases 851 of the side and leading lobes 850 to increase the flexibility of the lobes. The trailing end 802 includes the receiving/attachment aperture 872 and the flanking guide apertures 871, as well as four more apertures 875 which are located in the vicinity of the lobe bases 851 of the trailing lobes 850. The apertures 871, 872, 875 may function together to reduce the bending stiffness of the perimeter wall 842 in the vicinity of the lobe bases 851 of the trailing lobes 850 to increase the flexibility of the lobes. Each aperture 875 is elongated along a side-to-side (right-left) direction. Preferably, the apertures 875 are enlarged toward their lateral (outboard) ends so that the enlargement coincides with each side of the lobe base 851. Preferably, the lateral ends of the apertures 875 are enlarged toward the first and second sides 820, 821, respectively as shown, again to coincide with each side of the lobe base 851. The illustrated apertures 875 represent one of a plurality of alternative aperture configurations for the 8 mm size implant 80. The illustrated aperture 875 resembles the aperture 975 of implant 90.

Referring to FIGS. 9A-F, implant 70 includes the following structures and/or features which may be as described above for implants 10, 40 and having related reference numbers: body 700, leading edge/end 701, trailing edge/end 702, first plane 705, second plane 706, central plane 707, centralized aperture 710, central axis 711, first side 720, second side 721, first perimeter 730, second perimeter 731, first edge 740, second edge 741, perimeter wall 742, lobe 750, lobe base 751, lobe terminus 752, lobe first width 753, lobe second width 754, lobe first thickness 755, lobe second thickness 756, lobe end region 758, side apertures 770, guide apertures 771, receiving/attachment aperture 772, and/or apertures 773. Implant 70 may optionally include one or more grippers, each with a gripper base and gripper terminus, each optionally associated with a divot, like gripper 160, 460, gripper base 161, 461, gripper terminus 162, 462, and divot 163 of implants 10, 40. The lobes 750 of implant 70 may include bone ingrowth and/or ongrowth features as depicted in FIGS. 1-6, such as pores, ridges, loops, holes, spaces, lobe apertures 774 as shown, grooves, or any known surface that increases purchase or grips on the adjacent bone. The lobe apertures 774 may be filled with porous material.

Implant 70 includes large side apertures 770 and a large aperture 773 in the leading end 701. These apertures 770, 773 reduce the bending stiffness of the perimeter wall 742 in the vicinity of the lobe bases 751 of the side and leading lobes 750 to increase the flexibility of the lobes. The trailing end 702 includes the receiving/attachment aperture 772 and the flanking guide apertures 771, as well as four more apertures 775 which are located in the vicinity of the lobe bases 751 of the trailing lobes 750. The apertures 771, 772, 775 may function together to reduce the bending stiffness of the perimeter wall 742 in the vicinity of the lobe bases 751 of the trailing lobes 750 to increase the flexibility of the lobes. Each aperture 775 is elongated along a side-to-side (right-left) direction. Although not shown in this example, the apertures 775 may preferably be enlarged toward their lateral (outboard) ends so that the enlargement coincides with each side of the lobe base 751. Although not shown in this example, the lateral ends of the apertures 775 may preferably be enlarged toward the first and second sides 720, 721, respectively, again to coincide with each side of the lobe base 751. The illustrated apertures 775 represent one of a plurality of alternative aperture configurations for the 7 mm size implant 70.

Referring to FIGS. 10A-F, implant 60 includes the following structures and/or features which may be as described above for implants 10, 40 and having related reference numbers: body 600, leading edge/end 601, trailing edge/end 602, first plane 605, second plane 606, central plane 607, centralized aperture 610, central axis 611, first side 620, second side 621, first perimeter 630, second perimeter 631, first edge 640, second edge 641, perimeter wall 642, lobe 650, lobe base 651, lobe terminus 652, lobe first width 653, lobe second width 654, lobe first thickness 655, lobe second thickness 656, lobe end region 658, side apertures 670, guide apertures 671, receiving/attachment aperture 672, and/or apertures 673. Implant 60 may optionally include one or more grippers, each with a gripper base and gripper terminus, each optionally associated with a divot, like gripper 160, 460, gripper base 161, 461, gripper terminus 162, 462, and divot 163 of implants 10, 40. The lobes 650 of implant 60 may include bone ingrowth and/or ongrowth features as depicted in FIGS. 1-6, such as pores, ridges, loops, holes, spaces, lobe apertures 674 as shown, grooves, or any known surface that increases purchase or grips on the adjacent bone. The lobe apertures 674 may be filled with porous material.

Implant 60 includes large side apertures 670 and a large aperture 673 in the leading end 601. These apertures 670, 673 reduce the bending stiffness of the perimeter wall 642 in the vicinity of the lobe bases 651 of the side and leading lobes 650 to increase the flexibility of the lobes. The trailing end 602 includes the receiving/attachment aperture 672 and the flanking guide apertures 671, as well as four more apertures 675 which are located in the vicinity of the lobe bases 651 of the trailing lobes 650. The apertures 671, 672, 675 may function together to reduce the bending stiffness of the perimeter wall 642 in the vicinity of the lobe bases 651 of the trailing lobes 650 to increase the flexibility of the lobes. Each aperture 675 is elongated along a side-to-side (right-left) direction. Although not shown in this example, the apertures 675 may preferably be enlarged toward their lateral (outboard) ends so that the enlargement coincides with each side of the lobe base 651. Although not shown in this example, the lateral ends of the apertures 675 may preferably be enlarged toward the first and second sides 620, 621, respectively, again to coincide with each side of the lobe base 651. The illustrated apertures 675 represent one of a plurality of alternative aperture configurations for the 6 mm size implant 60. The illustrated aperture 675 resembles the aperture 775 of implant 70.

Referring to FIGS. 11A-F, implant 50 includes the following structures and/or features which may be as described above for implants 10, 40 and having related reference numbers: body 500, leading edge/end 501, trailing edge/end 502, first plane 505, second plane 506, central plane 507, centralized aperture 510, central axis 511, first side 520, second side 521, first perimeter 530, second perimeter 531, first edge 540, second edge 541, perimeter wall 542, lobe 550, lobe base 551, lobe terminus 552, lobe first width 553, lobe second width 554, lobe first thickness 555, lobe second thickness 556, lobe end region 558, side apertures 570, guide apertures 571, receiving/attachment aperture 572, and/or apertures 573. Implant 50 may optionally include one or more grippers, each with a gripper base and gripper terminus, each optionally associated with a divot, like gripper 160, 460, gripper base 161, 461, gripper terminus 162, 462, and divot 163 of implants 10, 40. The lobes 550 of implant 50 may include bone ingrowth and/or ongrowth features as depicted in FIGS. 1-6, such as pores, ridges, loops, holes, spaces, lobe apertures 574 as shown, grooves, or any known surface that increases purchase or grips on the adjacent bone. The lobe apertures 574 may be filled with porous material.

Implant 50 includes side apertures 570. This example lacks an aperture in the leading end 501 due to the implant's small size. The apertures 570 reduce the bending stiffness of the perimeter wall 542 in the vicinity of the lobe bases 551 of the side lobes 550 to increase the flexibility of the lobes. The trailing end 502 includes the receiving/attachment aperture 572 and the flanking guide apertures 571. In this example, the apertures 575 located in the vicinity of the lobe bases 551 of the trailing lobes 550 are merged with the guide apertures 571 so that there is a single aperture 571, 575 on either side of the receiving/attachment aperture 572, due to the small size of the implant. The apertures 571, 575, 572 may function together to reduce the bending stiffness of the perimeter wall 542 in the vicinity of the lobe bases 551 of the trailing lobes 550 to increase the flexibility of the lobes. Each aperture 571, 575 is elongated along a side-to-side (right-left) direction. Although not shown in this example, the apertures 571, 575 may preferably be enlarged toward their lateral (outboard) ends so that the enlargement coincides with each side of the lobe base 551. Although not shown in this example, the lateral ends of the apertures 571, 575 may preferably be enlarged toward the first and second sides 520, 521, respectively, again to coincide with each side of the lobe base 551. The illustrated apertures 571, 575 represent one of a plurality of alternative aperture configurations for the 5 mm size implant 50.

Figure 12:
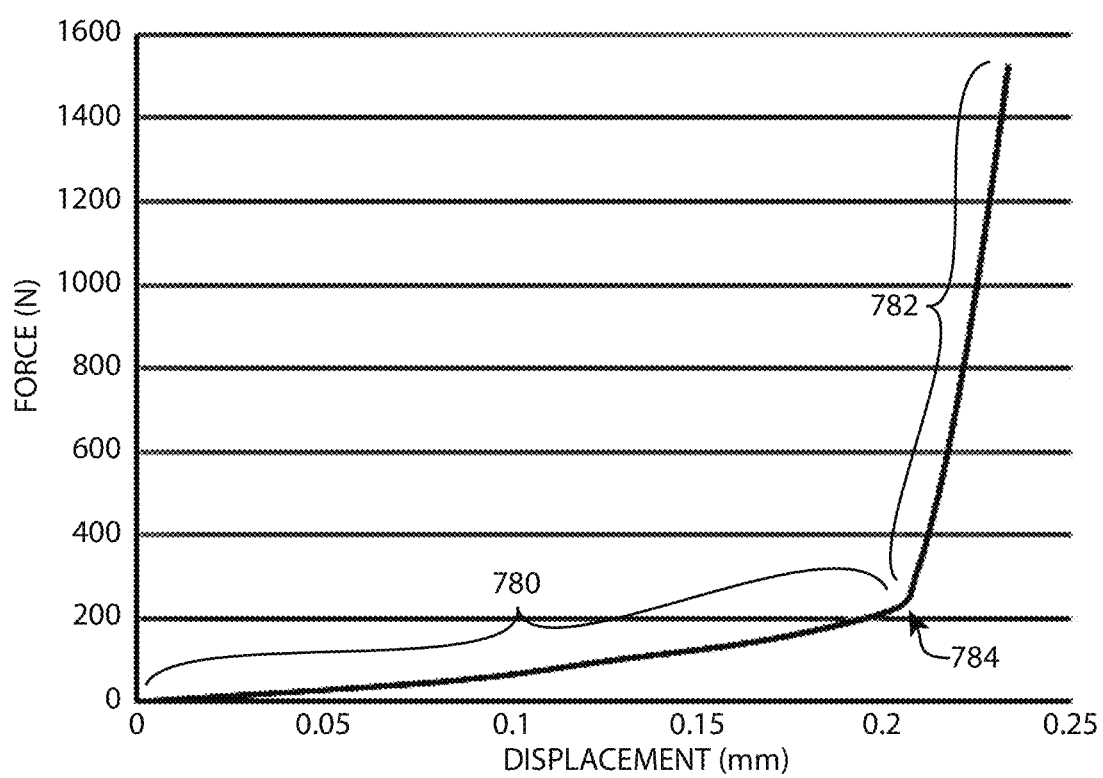
FIG. 12 is a graph of force versus displacement by finite element analysis of the implant of FIG. 9A.

Referring to FIG. 12, a force versus displacement curve is shown for a first variant of the 7 mm implant 70 of FIG. 9A. The curve was generated by finite element analysis. The curve includes a first portion 780 for loads less than or equal to 200 N and displacements less than or equal to 0.2 mm and a second portion 782 for loads greater than 300 N and displacements greater than 0.21 mm. The first portion 780 represents the implant bearing load primarily through the lobes. The second portion 782 represents the implant bearing load primarily through the perimeter wall. The second slope is greater than the first slope. A knee 784 or change in slope is located between the first and second portions 780, 782. These features are characteristic of the force versus displacement curves for the implants 50, 60, 70, 80, 90. The first portion 780 may have a slope of 1069 N/mm and an $R^2$ value of 0.9363. The second portion 782 may have a slope of 40,177 N/mm and an $R^2$ value of 0.9661.

Figure 13:
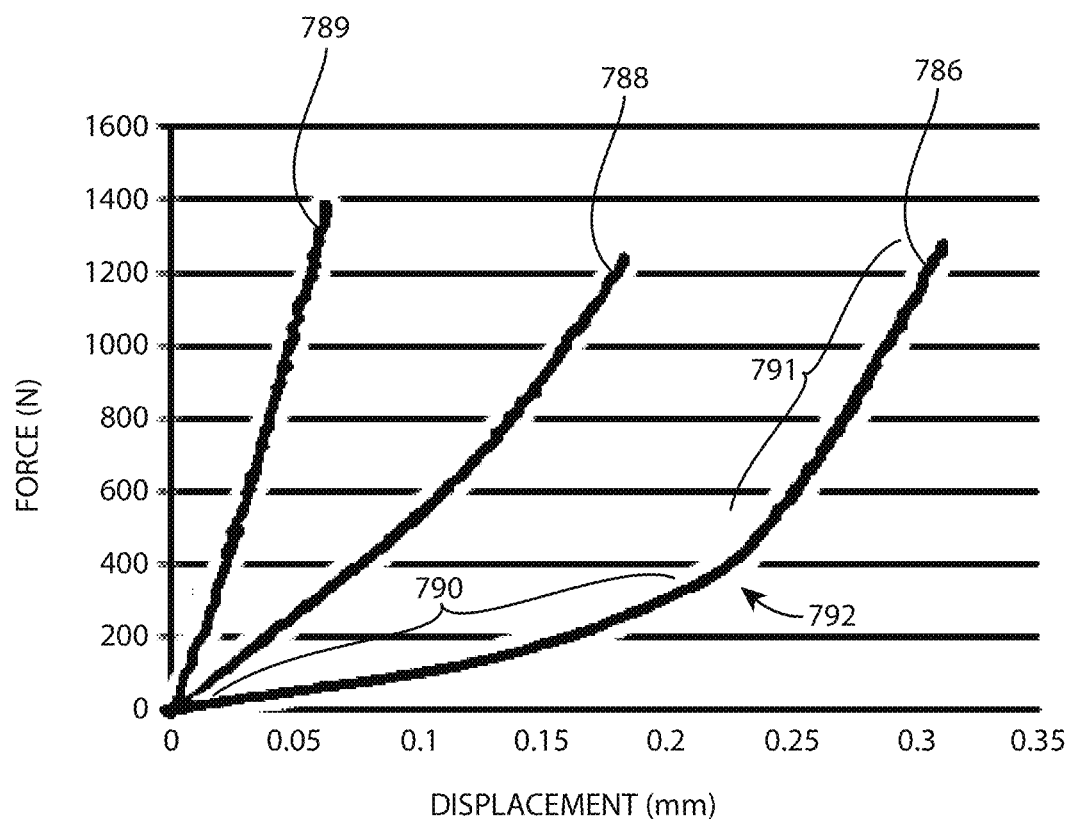
FIG. 13 is a graph of force versus displacement for the implant of FIG. 9A, a conventional PEEK intervertebral spacer, and a conventional titanium intervertebral spacer, all the same size.

Referring to FIG. 13, three force versus displacement curves are shown. The curve 786 is for a second variant of the 7 mm implant 70 of FIG. 9A. The curve 788 is for a 7 mm conventional PEEK implant. The curve 789 is for a 7 mm conventional titanium implant.

The curve 786 includes a first portion 790 for loads less than or equal to 300 N and displacements less than or equal to 0.2 mm and a second portion 791 for loads greater than 400 N and displacements greater than 0.23 mm. The first portion 790 represents the implant bearing load primarily through the lobes. The second portion 791 represents the implant bearing load primarily through the perimeter wall. The second slope is greater than the first slope. A knee 792 or change in slope is located between the first and second portions 791, 791. The first portion 790 may have a slope of 1333 N/mm and an $R^2$ value of 0.9683. The second portion 791 may have a slope of 10,274 N/mm and an $R^2$ value of 0.9917. The knee 792 of curve 786 is more gradual than the knee 784 of FIG. 12.

The curve 788 may have a slope of 6283 N/mm and an $R^2$ value of 0.9873.

The curve 789 may have a slope of 20,909 N/mm and an $R^2$ value of 0.995.

Figure 14A:
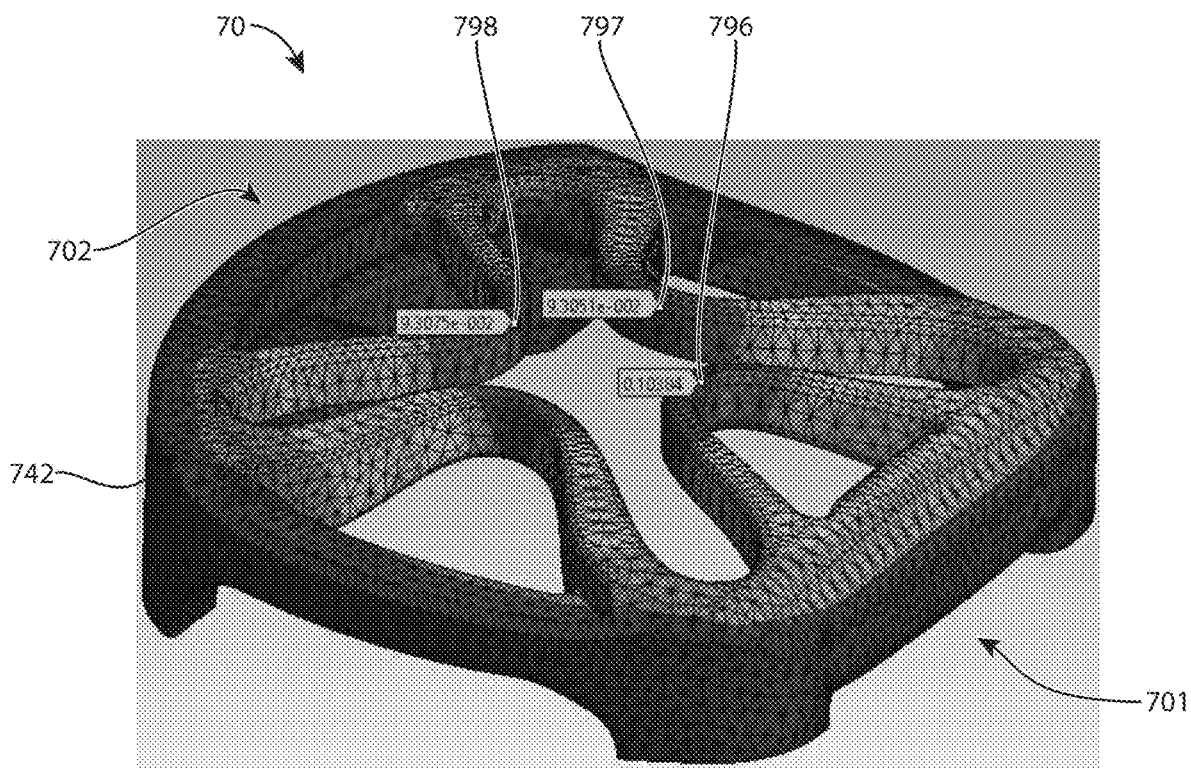
FIG. 14A is a finite element analysis contour plot of deformation of the implant of FIG. 9A under load.
Figure 14B:
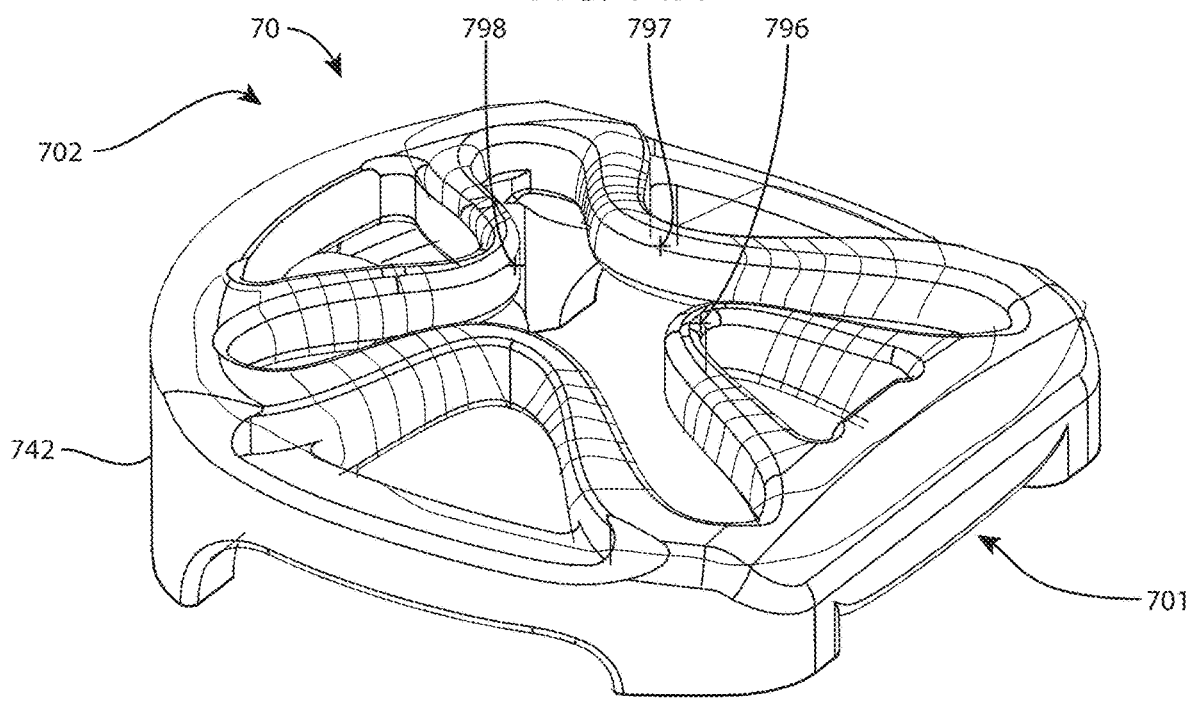
FIG. 14B is a line drawing corresponding to FIG. 14A, with iso-deflection lines.

Referring to FIGS. 14A and 14B, the superior half of the 7 mm implant 70 of FIG. 9A is shown in a finite element analysis color gradient plot (FIG. 14A) and again in FIG. 14B with iso-deflection lines instead of the color plot. The perimeter wall 742 has 0 mm displacement. The terminus 752 of the leading lobe 750 has a displacement of 0.10384 mm at point 796. The terminus of the right lobe has a displacement of 0.093051 mm at point 797; the left lobe is a mirror image of the right lobe and has the same displacement. The terminus of the trailing lobe has a displacement of 0.093075 mm at point 798. Thus, the displacement at point 797 is 89.6% of the displacement at point 796 (within 10%), and the displacement at point 796 is 111.6% of the displacement at point 797 (within 12%).

Any methods disclosed herein comprise one or more steps or actions for performing the described method. The method steps and/or actions may be interchanged with one another and applicable to all embodiments of the intervertebral body implants described herein. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the invention.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

The invention claimed is:

1. An intervertebral spacer implant comprising:
a body comprising:
a first side configured to contact a first vertebra;
a second side opposite the first side and configured to contact a second vertebra adjacent to the first vertebra;
a perimeter wall extending around the body between the first and second sides and comprising an aperture; and
a hollow interior enclosed by the perimeter wall between the first and second sides;
wherein the hollow interior is in communication with the aperture of the perimeter wall but does not extend into the perimeter wall;
wherein the first side is configured to flex, such that, with the body implanted between the first vertebra and the second vertebra, in response to pressure between the first vertebra and the second vertebra, a central portion of the first side moves, relative to the perimeter wall, into the hollow interior;
wherein the first side comprises a first cantilevered member comprising:
a first base adjacent to the perimeter wall; and
a first end region extending away from the first base and the perimeter wall, and into the central portion; and
the first cantilevered member flexes in response to the pressure such that the first end region moves into the hollow interior; and
wherein the first side further comprises a second cantilevered member comprising:
a second base adjacent to the perimeter wall; and
a second end region extending away from the second base and the perimeter wall, and into the central portion; and
the second cantilevered member flexes, independently of the first cantilevered member, in response to the pressure such that the second end region moves into the hollow interior.

2. The intervertebral spacer implant of claim 1, wherein the body further comprises a centralized aperture extending through the first side, the second side, and the hollow interior.

3. The intervertebral spacer implant of claim 1, wherein:
the second side comprises a third cantilevered member comprising:
a third base adjacent to the perimeter wall; and
a third end region extending away from the third base and the perimeter wall;
the third cantilevered member flexes in response to the pressure such that the third end region moves into the hollow interior;
the second side further comprises a fourth cantilevered member comprising:
a fourth base adjacent to the perimeter wall; and
a fourth end region extending away from the fourth base and the perimeter wall; and
the fourth cantilevered member flexes in response to the pressure such that the fourth end region moves into the hollow interior.

4. The intervertebral spacer implant of claim 1, wherein the first side further comprises a first stiffness that is equal to or less than a compressive modulus of cancellous bone.

5. The intervertebral spacer implant of claim 4, wherein:
the first stiffness is applicable to a first level of flexure of the first side; and
the first side further comprises a second stiffness, greater than the first stiffness, that is applicable to a second level, greater than the first level, of flexure of the first side.

6. The intervertebral spacer implant of claim 5, wherein the second level of flexure of the first side commences when the pressure exceeds about 200 N.

7. The intervertebral spacer implant of claim 1, wherein the perimeter wall comprises an aperture configured such that, with the body implanted between the first vertebra and the second vertebra, in response to pressure between the first vertebra and the second vertebra, the perimeter wall flexes.

8. The intervertebral spacer implant of claim 7, wherein:
the aperture is positioned adjacent to the first base such that flexure of the perimeter wall facilitates pivotal motion of the first base.

9. An intervertebral spacer implant comprising:
a body comprising:
a first side configured to contact a first vertebra;
a second side opposite the first side and configured to contact a second vertebra adjacent to the first vertebra;
a perimeter wall extending around the body between the first and second sides; and
a hollow interior extending through the body between the first and second sides;
wherein the first side extends to cover at least part of the hollow interior;
wherein the perimeter wall comprises an aperture configured such that, with the body implanted between the first vertebra and the second vertebra, in response to pressure between the first vertebra and the second vertebra, an edge of the perimeter wall rotates;
wherein the first side is configured to flex, such that, with the body implanted between the first vertebra and the second vertebra, in response to the pressure, a central portion of the first side moves, relative to the perimeter wall, into the hollow interior;
wherein the first side comprises a first cantilevered member comprising:
a first base adjacent to the perimeter wall; and
a first end region extending away from the first base and the perimeter wall, and into the central portion; and
the first cantilevered member flexes in response to the pressure such that the first end region moves into the hollow interior; and
wherein the aperture is positioned adjacent to the first base such that flexure of the perimeter wall facilitates pivotal motion of the first base.

10. The intervertebral spacer implant of claim 9, wherein the aperture comprises an elongated shape generally perpendicular to a central axis of the body.

11. The intervertebral spacer implant of claim 9, wherein:
the perimeter wall comprises:
a first lateral side comprising the aperture;
a second lateral side comprises a second aperture;
an anterior side; and
a posterior side; and the anterior side and the posterior side each lack apertures configured to provide flexure of the anterior side and the posterior side in response to the pressure.

12. An intervertebral spacer implant comprising:
a body comprising:
  a first side configured to contact a first vertebra;
  a second side opposite the first side and configured to contact a second vertebra adjacent to the first vertebra;
  a perimeter wall extending around the body between the first and second sides wherein the first side extends superiorly above the perimeter wall; and
  a hollow interior circumscribed by the perimeter wall and extending through the body from the first side to the second side;
wherein the perimeter wall comprises:
  a first lateral side comprising a first aperture;
  a second lateral side comprises a second aperture;
  an anterior side; and
  a posterior side;
wherein the first aperture and the second aperture are configured such that, with the body implanted between the first vertebra and the second vertebra, in response to pressure between the first vertebra and the second vertebra, the first lateral side and the second lateral side flex;
wherein the anterior side and the posterior side each lack apertures configured to provide flexure of the anterior side and the posterior side in response to the pressure;
wherein the first side is configured to flex, such that, with the body implanted between the first vertebra and the second vertebra, in response to the pressure, a central portion of the first side moves, relative to the perimeter wall, into the hollow interior; and
wherein the first side comprises a first cantilevered member comprising:
  a first base adjacent to and extending parallel to the first aperture; and
  a first end region extending away from the first base and the perimeter wall, and into the central portion;
the first cantilevered member flexes in response to the pressure such that the first end region moves into the hollow interior;
the second side comprises a second cantilevered member comprising:
  a second base adjacent to and extending parallel to the second aperture; and
  a second end region extending away from the second base and the perimeter wall, and into the central portion; and
the second cantilevered member flexes, independently of the first cantilevered member, in response to the pressure such that the second end region moves into the hollow interior.

13. The intervertebral spacer implant of claim 12, wherein:
the first aperture is positioned such that flexure of the first lateral side facilitates pivotal motion of the first base; and
the second aperture is positioned such that flexure of the second lateral side facilitates pivotal motion of the second base.

* * * * *